US010550427B2

(12) United States Patent
Schupp et al.

(10) Patent No.: US 10,550,427 B2
(45) Date of Patent: Feb. 4, 2020

(54) SYSTEMS AND METHODS FOR UNIVERSAL TAIL-BASED INDEXING STRATEGIES FOR AMPLICON SEQUENCING

(71) Applicants: THE TRANSLATIONAL GENOMICS RESEARCH INSTITUTE, Phoenix, AZ (US); ARIZONA BOARD OF REGENTS ON BEHALF OF NORTHERN ARIZONA UNIVERSITY, Flagstaff, AZ (US)

(72) Inventors: James M. Schupp, Phoenix, AZ (US); Rebecca E. Colman, Phoenix, AZ (US); David Engelthaler, Phoenix, AZ (US); John Gillece, Phoenix, AZ (US); Nathan Hicks, Phoenix, AZ (US); Paul S. Keim, Phoenix, AZ (US)

(73) Assignees: The Translational Genomics Research Institute, Phoenix, AZ (US); Arizona Board of Regents on behalf of Northern Arizona University, Flagstaff, AZ (US)

( * ) Notice: Subject to any disclaimer, the term of this patent is extended or adjusted under 35 U.S.C. 154(b) by 424 days.

(21) Appl. No.: 15/034,544

(22) PCT Filed: Nov. 10, 2014

(86) PCT No.: PCT/US2014/064890
§ 371 (c)(1),
(2) Date: May 4, 2016

(87) PCT Pub. No.: WO2015/070187
PCT Pub. Date: May 14, 2015

(65) Prior Publication Data
US 2016/0326572 A1    Nov. 10, 2016

Related U.S. Application Data

(60) Provisional application No. 61/902,432, filed on Nov. 11, 2013.

(51) Int. Cl.
*C12P 19/34* (2006.01)
*C12Q 1/686* (2018.01)
*C12Q 1/6874* (2018.01)

(52) U.S. Cl.
CPC .......... *C12Q 1/686* (2013.01); *C12Q 1/6874* (2013.01)

(58) Field of Classification Search
CPC ............. C12Q 1/686; C12Q 2525/155; C12Q 2525/191; C12Q 2537/143; C12Q 1/6869; C12Q 1/6874
USPC ....................................................... 435/91.2
See application file for complete search history.

(56) References Cited

U.S. PATENT DOCUMENTS

| | | | |
|---|---|---|---|
| 7,754,429 B2 | 7/2010 | Rigatti et al. | |
| 8,431,348 B2 | 4/2013 | Rigatti et al. | |
| 2009/0042196 A1* | 2/2009 | Guo | C12Q 1/6858 435/6.11 |
| 2011/0136116 A1* | 6/2011 | Barany | C12Q 1/6827 435/6.11 |
| 2012/0220494 A1* | 8/2012 | Samuels | C12N 15/1075 506/16 |
| 2013/0137587 A1 | 5/2013 | Van Eijk et al. | |
| 2013/0143794 A1 | 6/2013 | Baker et al. | |

FOREIGN PATENT DOCUMENTS

WO        2005/042759 A2    5/2005

OTHER PUBLICATIONS

Price et al., Electrophoresis., 31 (23-24): 3881-3888, Dec. (Year: 2010).*
Kozich et al., Applied and Environmental Microbiology, 79 (17): 5112-5120, Jun. (Year: 2013).*
Kowarewa and Turner., Methods in Molecular Biology, vol. 733, pp. 279-298 (Year: 2011).*
Gholami et al., Plant Biotechnology Journal, vol. 10, pp. 635-645, (Year: 2012).*
Caporaso, J. G., et al. Ultra-high-throughput microbial community analysis on the Illumina HiSeq and MiSeq platforms. ISME J. Aug. 2012; 6(8): 1621-1624. doi: 10.1038/ismej.2012.8. PMCID: PMC3400413.
Chubiz, L. M., et al. FREQ-Seq: A Rapid, Cost-Effective, Sequencing-Based Method to Determine Allele Frequencies Directly from Mixed Populations. PLoS One 2012; 7(10): e47959. doi: 10.1371/journal.pone.0047959. PMCID: PMC3485326.
Chamberlin, et al. New RNA polymerase from *Escherichia coli* infected with bacteriophage T7. Nature1970; 228:227-231.
Wu, et al. The ligation amplification reaction (LAR)—amplification of specific DNA sequences using sequential rounds of template-dependent ligation. Genomics1989; 4:560-569.
U'ren, et al. Tandem repeat regions within the Burkholderia pseudomallei genome and their application for high resolution genotyping. BMC Microbiol. 2007; 7:23. doi: 10.1186/1471-2180-7-23.
World Health Organization. Global Tuberculosis Report 2013. World health Organization (Geneva Switzerland) 2013; Report WHO/HTM/TB/2013.11; ISBN 9789241564656.
Rodwell, et al. Predicting Extensively Drug-resistant Tuberculosis (XDR-TB) Phenotypes with Genetic Mutations. J Clin Microbiol. 2013; 52(3)781-789.

(Continued)

*Primary Examiner* — Cynthia B Wilder
(74) *Attorney, Agent, or Firm* — Rodney J. Fuller; Booth Udall Fuller, PLC

(57) ABSTRACT

Some embodiments of the invention include a method of preparing a sample for sequencing that includes receiving a sample and amplifying at least one marker within the sample. In some embodiments, amplification of the first marker may include mixing the sample with a first oligonucleotide that comprises a first universal tail sequence and a second oligonucleotide that comprises a second universal tail sequence. In some aspects of the invention, the first universal tail sequence and the second universal tail sequence are different sequences.

18 Claims, 15 Drawing Sheets

Specification includes a Sequence Listing.

(56) References Cited

OTHER PUBLICATIONS

Johnson, et al. Drug susceptibility testing using molecular techniques can enhance tuberculosis diagnosis. Journal of infection in developing countries 2008; 2(1):40-45.
Neonakis, et al. Molecular diagnostic tools in mycobacteriology. J Microbiol Methods 2008; 75(1):1-11.
Rinder, et al. Heteroresistance in Mycobacterium tuberculosis. Int J Tuberc Lung Dis 2001; 5(4):339-345.
Tolani, et al. Drug resistance mutations and heteroresistance detected using the GenoType MTBDRplus assay and their implication for treatment outcomes in patients from Mumbai, India. BMC Infectious Diseases 2012; 12:9.
Hofmann, et al. Mechanisms of heteroresistance to isoniazid and rifampin of Mycobacterium tuberculosis in Tashkent, Uzbekistan. The European Respiratory Journal 2009; 33(2):368-374.
Folkvardsen, et al. Rifampin heteroresistance in Mycobacterium tuberculosis cultures as detected by phenotypic and genotypic drug susceptibility test methods. J Clin Microbiol 2013; 51(12):4220-4222.
Chakrovorty, et al. Rapid detection of fluoroquinolone-resistant and heteroresistant Mycobacterium tuberculosis by use of sloppy molecular beacons and dual melting-temperature codes in a real-time PCR assay. J Clin Microbiol 2011; 49(3):932-940.
Blankemore, et al. Evaluation of the analytical performance of the Xpert MTB/RIF assay. J Clin Microbiol 2010; 48 (7):2495-2501.
Pholwat, et al. Digital PCR to detect and quantify heteroresistance in drug resistant Mycobacterium tuberculosis. PLoS ONE 2013; 8(2):e57238.
Telenti, et al. Genotypic assessment of isoniazid and rifampin resistance in Mycobacterium tuberculosis: a blind study at reference laboratory level. J Clin Microbiol 1997; 35(3):719-723.
Kim, et al. Detection of rifampin-resistant Mycobacterium tuberculosis in sputa by nested PCR-linked single-strand conformation polymorphism and DNA sequencing. J Clin Microbiol 2001; 39(7):2610-2617.
Piatek, et al. Genotypic analysis of Mycobacterium tuberculosis in two distinct populations using molecular beacons: implications for rapid susceptibility testing. Antimicrob Agents Chemother 2000; 44(1):103-110.
Pholwat, et al. Integrated Microfluidic Card with Taq-Man Probes and High-Resolution Melt Analysis To Detect Tuberculosis Drug Resistance Mutations across 10 Genes. mBio 2015; 6(2):1-9.
Campbell, et al. Molecular detection of mutations associated with first- and second-line drug resistance compared with conventional drug susceptibility testing of Mycobacterium tuberculosis. Antimicrob Agents Chemother 2011; 55 (5):2032-2041.
Koser, et al. Whole-genome sequencing for rapid susceptibility testing of M. tuberculosis. N Engl J Med 2013; 369 (3):290-292.
Lin, et al. Pyrosequencing for rapid detection of extensively drug-resistant Mycobacterium tuberculosis in clinical isolates and clinical specimens. J Clin Microbiol 2014; 52(2):475-482.
Zhang, et al. Subpopulation analysis of heteroresistance to fluoroquinolone in Mycobacterium tuberculosis isolates from Beijing, China. J Clin Microbiol. 2012; 50(4):1471-1474.
Ajbani, et al. Evaluation of genotype MTBDRsl assay to detect drug resistance associated with fluoroquinolones, aminoglycosides and ethambutol on clinical sediments. PLoS One 2012; 7(11):e49433.
Duwe, et al. A new and rapid genotypic assay for the detection of neuraminidase inhibitor resistant influenza A viruses of subtype H1N1, H3N2, and H5N1. Journal of virological methods 2008; 153(2):134-141.
Kircher, M., et al. Double indexing overcomes inaccuracies in multiplex sequencing on the Illumina platform. Nucleic Acids Res 2012; 40(1):e3.
Schmitt, et al. Detection of ultra-rare mutations by next-generation sequencing. Proc Natl Acad Sci U S A 2012; 109 (36):14508-14513.
Hedskog, et al. Dynamics of HIV-1 quasispecies during antiviral treatment dissected using ultra-deep pyrosequencing. PLoS One 2010; 5(7):e11345.
Mild, et al. Performance of ultra-deep pyrosequencing in analysis of HIV-1 pol gene variation. PLoS One 2011; 6(7): e22741.
Zhou, et al. Prevention, diagnosis and treatment of high-throughput sequencing data pathologies. Mol Ecol 2014; 23 (7):1679-1700.
Watson, et al. Viral population analysis and minority-variant detection using short read next-generation sequencing. Philos Trans R Soc Lond B Biol Sci 2013; 368(1614):20120205.
Zagordi, et al. Error correction of next-generation sequencing data and reliable estimation of HIV quasispecies. Nucleic Acids Res 2010; 38(21):7400-7409.
MacAlalad, et al. Highly sensitive and specific detection of rare variants in mixed viral populations from massively parallel sequence data. PLoS computational biology 2012; 8(3):e1002417.
Lou, et al. High-throughput DNA sequencing errors are reduced by orders of magnitude using circle sequencing. Proc Natl Acad Sci U S A 2013; 110(49):19872-19877.
Chen-Harris, et al. Ultra-deep mutant spectrum profiling: improving sequencing accuracy using overlapping read pairs. BMC Genomics 2013; 14(1):96.
Menzel, et al. Comprehensive evaluation and optimization of amplicon library preparation methods for high-throughput antibody sequencing. PLoS One 2014; 9(5):e96727.
Wu, et al. HIV-1 quasispecies delineation by tag linkage deep sequencing. PLoS One 2014; 9(5):e97505.
Garfein, et al. Phenotypic and Genotypic Diversity in a Multinational Sample of Drug-resistant M. tuberculosis Isolates. The International Journal of Tuberculosis and Lung Disease (2014); 19(4):420-427.
Hillery, et al. The Global Consortium for Drug-resistant Tuberculosis Diagnostics (GCDD): Design for a multi-site study of rapid tests to detect extensively drug-resistant tuberculosis. Trials 2014; 15:434.
World Health Organization. Policy guidance on drug-susceptibility testing (DST) of second-line antituberculosis drugs. World Health Organization (Geneva, Switzerland) 2008; Report WHO/HTM/TB/2008.392.
Lin, et al. Multicenter evaluation of Bactec MGIT 960 system for second-line drug susceptibility testing of Mycobacterium tuberculosis complex. J Clin Microbiol 2009; 47(11):3630-3634.
Rodrigues, et al. Drug susceptibility testing of Mycobacterium tuberculosis against second-line drugs using the Bactec MGIT 960 System. The International Journal of Tuberculosis and Lung Disease 2008; 12(12):1449-1455.
Georghiou, et al. Evaluation of Genetic Mutations Associated with Mycobacterium tuberculosis Resistance to Amikacin, Kanamycin and Capreomycin: A Systematic Review. PLoS One 2012; 7(3):e33275.
Maruri, et al. A systematic review of gyrase mutations associated with fluoroquinolone-resistant Mycobacterium tuberculosis and a proposed gyrase numbering system. Journal of Antimicrobial Chemotherapy 2012; 67(4):819-831.
Sandgren, et al. Tuberculosis Drug Resistance Mutation Database. PLoS Med 2009; 6(2):e1000002.
Kozarewa, et al. 96-Plex Molecular Barcoding for the Illumina Genome Analyzer. High-Throughput Next Generation Sequencing. Methods in Molecular Biology 2011; 733:279-298.
Lui, et al. BactQuant: An enhanced broad-coverage bacterial quantitative real-time PCR assay. BMC Microbiology 2012; 12(1):56.
Lohse, et al. RobiNA: a user-friendly, integrated software solution for RNA-Seq-based transcriptomics. Nucleic Acids Res 2012; 40:W622-W627.
Homs, et al. Clinical application of estimating hepatitis B virus quasispecies complexity by massive sequencing: correlation between natural evolution and on-treatment evolution. PLoS One 2014; 9(11):e112306.
McElroy, et al. Accurate single nucleotide variant detection in viral populations by combining probabilistic clustering with a statistical test of strand bias. BMC Genomics 2013; 14:501.
Bashford-Rogers, et al. Capturing needles in haystacks: a comparison of B-cell receptor sequencing methods. BMC immunology 2014; 15(1):29.
Eldholm, et al. Evolution of extensively drug-resistant Mycobacterium tuberculosis from a susceptible ancestor in a single patient. Genome biology 2014; 15(11):490.

(56) References Cited

OTHER PUBLICATIONS

Kirkness et al., "The dog genome: survey sequencing and comparative analysis", Science, 301:1898-1903 (Sep. 26, 2003).
Delong et al., "Community Genomics Among Stratified Microbial Assemblages in the Ocean's Interior", Science, 311:496-503 (Jan. 27, 2006).
International Search Report for PCT/2014/064890 dated Mar. 3, 2015.
Written Opinion of the International Searching Authority for PCT/US2014/064890 dated Mar. 3, 2015.
International Preliminary Report on Patentability for PCT/US2014/064890 dated May 17, 2016.

* cited by examiner

Name   Sequence (5'-3')
UT1    ACCCAACTGAATGGAGC (SEQ ID NO: 1)
UT2    ACGCACTTGACTTGTCTTC (SEQ ID NO: 2)
UT3    ATCGACTGTGTTAGGTCAC (SEQ ID NO: 3)
UT4    CTGTCCTTACCTCAATCTC (SEQ ID NO: 4)

Common UT1 oligonucleotide
AATGATACGGCGACCACCGAGATCTACACTATGGT
AATTGTACCCAACTGAATGGAGC (SEQ ID NO: 5)

UT1 Read 1 seq primer
CCGAGATCTACACTATGGTAATTGT**ACCCAACTGA
ATGGAGC** (SEQ ID NO: 6)

UT2 index read seq primer
GAAGACAAGTCAAGTGCGTGGCTGACTGACT (SEQ ID NO: 7)

UT2 read 2 seq primer
AGTCAGTCAGCCACGCACTTGACTTGTCTTC (SEQ ID NO: 8)

FIGURE 2

Universal tail index oligo sequences

Indexed -UT2-1 (SEQ ID NO: 9)
CAAGCAGAAGACGGCATACGAGATACAAGCTAAGTCAGTCAGCCACGCACTTGACTTGTCTTC Indexed -UT2-2 (SEQ ID NO: 10)
CAAGCAGAAGACGGCATACGAGATAAACATCGAGTCAGTCAGCCACGCACTTGACTTGTCTTC Indexed -UT2-3 (SEQ ID NO: 11)
CAAGCAGAAGACGGCATACGAGATACATTGGCAGTCAGTCAGCCACGCACTTGACTTGTCTTC Indexed -UT2-4 (SEQ ID NO: 12)
CAAGCAGAAGACGGCATACGAGATACCACTGTAGTCAGTCAGCCACGCACTTGACTTGTCTTC Indexed -UT2-5 (SEQ ID NO: 13)
CAAGCAGAAGACGGCATACGAGATAACGTGATAGTCAGTCAGCCACGCACTTGACTTGTCTTC Indexed -UT2-6 (SEQ ID NO: 14)
CAAGCAGAAGACGGCATACGAGATCGCTGATCAGTCAGTCAGCCACGCACTTGACTTGTCTTC Indexed -UT2-7 (SEQ ID NO: 15)
CAAGCAGAAGACGGCATACGAGATCAGATCTGAGTCAGTCAGCCACGCACTTGACTTGTCTTC Indexed -UT2-8 (SEQ ID NO: 16)
CAAGCAGAAGACGGCATACGAGATATGCCTAAAGTCAGTCAGCCACGCACTTGACTTGTCTTC Indexed -UT2-10 (SEQ ID NO: 17)
CAAGCAGAAGACGGCATACGAGATAGTACAAGAGTCAGTCAGCCACGCACTTGACTTGTCTTC Indexed -UT2-11 (SEQ ID NO: 18)
CAAGCAGAAGACGGCATACGAGATCATCAAGTAGTCAGTCAGCCACGCACTTGACTTGTCTTC Indexed -UT2-12 (SEQ ID NO: 19)
CAAGCAGAAGACGGCATACGAGATAGTGGTCAAGTCAGTCAGCCACGCACTTGACTTGTCTTC Indexed -UT2-13 (SEQ ID NO: 20)
CAAGCAGAAGACGGCATACGAGATAACAACCAAGTCAGTCAGCCACGCACTTGACTTGTCTTC Indexed -UT2-37 (SEQ ID NO: 21)
CAAGCAGAAGACGGCATACGAGATCCGAAGTAAGTCAGTCAGCCACGCACTTGACTTGTCTTC Indexed -UT2-38 (SEQ ID NO: 22)
CAAGCAGAAGACGGCATACGAGATCCGTGAGAAGTCAGTCAGCCACGCACTTGACTTGTCTTC

FIGURE 2 (Continued)

Universal tail index oligo sequences

Indexed -UT2-39 (SEQ ID NO: 23)
CAAGCAGAAGACGGCATACGAGATCCTCCTGAAGTCAGTCAGCCACGCACTTGACTTGTCTTC Indexed -UT2-40 (SEQ ID NO: 24)
CAAGCAGAAGACGGCATACGAGATCGAACTTAAGTCAGTCAGCCACGCACTTGACTTGTCTTC Indexed -UT2-41 (SEQ ID NO: 25)
CAAGCAGAAGACGGCATACGAGATCGACTGGAAGTCAGTCAGCCACGCACTTGACTTGTCTTC Indexed -UT2-42 (SEQ ID NO: 26)
CAAGCAGAAGACGGCATACGAGATCGCATACAAGTCAGTCAGCCACGCACTTGACTTGTCTTC Indexed -UT2-43 (SEQ ID NO: 27)
CAAGCAGAAGACGGCATACGAGATCTCAATGAAGTCAGTCAGCCACGCACTTGACTTGTCTTC Indexed -UT2-44 (SEQ ID NO: 28)
CAAGCAGAAGACGGCATACGAGATCTGAGCCAAGTCAGTCAGCCACGCACTTGACTTGTCTTC Indexed -UT2-45 (SEQ ID NO: 29)
CAAGCAGAAGACGGCATACGAGATCTGGCATAAGTCAGTCAGCCACGCACTTGACTTGTCTTC Indexed -UT2-46 (SEQ ID NO: 30)
CAAGCAGAAGACGGCATACGAGATGAATCTGAAGTCAGTCAGCCACGCACTTGACTTGTCTTC Indexed -UT2-47 (SEQ ID NO: 31)
CAAGCAGAAGACGGCATACGAGATGACTAGTAAGTCAGTCAGCCACGCACTTGACTTGTCTTC Indexed -UT2-48 (SEQ ID NO: 32)
CAAGCAGAAGACGGCATACGAGATGAGCTGAAAGTCAGTCAGCCACGCACTTGACTTGTCTTC Indexed -UT2-49 (SEQ ID NO: 33)
CAAGCAGAAGACGGCATACGAGATGATAGACAAGTCAGTCAGCCACGCACTTGACTTGTCTTC Indexed -UT2-50 (SEQ ID NO: 34)
CAAGCAGAAGACGGCATACGAGATGCCACATAAGTCAGTCAGCCACGCACTTGACTTGTCTTC Indexed -UT2-51 (SEQ ID NO: 35)
CAAGCAGAAGACGGCATACGAGATGCGAGTAAAGTCAGTCAGCCACGCACTTGACTTGTCTTC Indexed -UT2-52 (SEQ ID NO: 36)
CAAGCAGAAGACGGCATACGAGATGCTAACGAAGTCAGTCAGCCACGCACTTGACTTGTCTTC

FIGURE 2 (Continued)

Universal tail index oligo sequences

Indexed -UT2-53 (SEQ ID NO: 37)
CAAGCAGAAGACGGCATACGAGATGCTCGGTAAGTCAGTCAGCCACGCACTTGACTTGTCTTC Indexed -UT2-54 (SEQ ID NO: 38)
CAAGCAGAAGACGGCATACGAGATGGAGAACAAGTCAGTCAGCCACGCACTTGACTTGTCTTC Indexed -UT2-55 (SEQ ID NO: 39)
CAAGCAGAAGACGGCATACGAGATGGTGCGAAAGTCAGTCAGCCACGCACTTGACTTGTCTTC Indexed -UT2-56 (SEQ ID NO: 40)
CAAGCAGAAGACGGCATACGAGATGTACGCAAAGTCAGTCAGCCACGCACTTGACTTGTCTTC Indexed -UT2-57 (SEQ ID NO: 41)
CAAGCAGAAGACGGCATACGAGATGTCGTAGAAGTCAGTCAGCCACGCACTTGACTTGTCTTC Indexed -UT2-58 (SEQ ID NO: 42)
CAAGCAGAAGACGGCATACGAGATGTCTGTCAAGTCAGTCAGCCACGCACTTGACTTGTCTTC Indexed -UT2-97 (SEQ ID NO: 43)
CAAGCAGAAGACGGCATACGAGATACTTGATGAGTCAGTCAGCCACGCACTTGACTTGTCTTC Indexed -UT2-98 (SEQ ID NO: 44)
CAAGCAGAAGACGGCATACGAGATTGACAGACAGTCAGTCAGCCACGCACTTGACTTGTCTTC

FIGURE 2 (Continued)

Internal Positive PCR and Sequencing Control for Universal Tail
Amplicon Sequencing

SEQUENCE LISTING

<160> NUMBER OF SEQ ID NOS: 72

<210> SEQ ID NO 1
<211> LENGTH: 17
<212> TYPE: DNA
<213> ORGANISM: Artificial Sequence
<220> FEATURE:
<223> OTHER INFORMATION: Primer

<400> SEQUENCE: 1
acccaactga atggagc                                                     17

<210> SEQ ID NO 2
<211> LENGTH: 19
<212> TYPE: DNA
<213> ORGANISM: Artificial Sequence
<220> FEATURE:
<223> OTHER INFORMATION: Primer

<400> SEQUENCE: 2
acgcacttga cttgtcttc                                                   19

<210> SEQ ID NO 3
<211> LENGTH: 19
<212> TYPE: DNA
<213> ORGANISM: Artificial Sequence
<220> FEATURE:
<223> OTHER INFORMATION: Primer

<400> SEQUENCE: 3
atcgactgtg ttaggtcac                                                   19

<210> SEQ ID NO 4
<211> LENGTH: 19
<212> TYPE: DNA
<213> ORGANISM: Artificial Sequence
<220> FEATURE:
<223> OTHER INFORMATION: Primer

<400> SEQUENCE: 4
ctgtccttac ctcaatctc                                                   19

<210> SEQ ID NO 5
<211> LENGTH: 58
<212> TYPE: DNA
<213> ORGANISM: Artificial Sequence
<220> FEATURE:
<223> OTHER INFORMATION: Primer

<400> SEQUENCE: 5
aatgatacgg cgaccaccga gatctacact atggtaattg tacccaactg aatggagc        58

<210> SEQ ID NO 6
<211> LENGTH: 42
<212> TYPE: DNA
<213> ORGANISM: Artificial Sequence
<220> FEATURE:
<223> OTHER INFORMATION: Primer

<400> SEQUENCE: 6
ccgagatcta cactatggta attgtaccca actgaatgga gc                         42

<210> SEQ ID NO 7
<211> LENGTH: 31
<212> TYPE: DNA
<213> ORGANISM: Artificial Sequence

```
<220> FEATURE:
<223> OTHER INFORMATION: Primer

<400> SEQUENCE: 7
gaagacaagt caagtgcgtg gctgactgac t                              31

<210> SEQ ID NO 8
<211> LENGTH: 31
<212> TYPE: DNA
<213> ORGANISM: Artificial Sequence
<220> FEATURE:
<223> OTHER INFORMATION: Primer

<400> SEQUENCE: 8
agtcagtcag ccacgcactt gacttgtctt c                              31

<210> SEQ ID NO 9
<211> LENGTH: 63
<212> TYPE: DNA
<213> ORGANISM: Artificial Sequence
<220> FEATURE:
<223> OTHER INFORMATION: Primer

<400> SEQUENCE: 9
caagcagaag acggcatacg agatacaagc taagtcagtc agccacgcac ttgacttgtc    60
ttc                                                                 63

<210> SEQ ID NO 10
<211> LENGTH: 63
<212> TYPE: DNA
<213> ORGANISM: Artificial Sequence
<220> FEATURE:
<223> OTHER INFORMATION: Primer

<400> SEQUENCE: 10
caagcagaag acggcatacg agataaacat cgagtcagtc agccacgcac ttgacttgtc    60
ttc                                                                 63

<210> SEQ ID NO 11
<211> LENGTH: 63
<212> TYPE: DNA
<213> ORGANISM: Artificial Sequence
<220> FEATURE:
<223> OTHER INFORMATION: Primer

<400> SEQUENCE: 11
caagcagaag acggcatacg agatacattg gcagtcagtc agccacgcac ttgacttgtc    60
ttc                                                                 63

<210> SEQ ID NO 12
<211> LENGTH: 63
<212> TYPE: DNA
<213> ORGANISM: Artificial Sequence
<220> FEATURE:
<223> OTHER INFORMATION: Primer

<400> SEQUENCE: 12
caagcagaag acggcatacg agataccact gtagtcagtc agccacgcac ttgacttgtc    60
ttc                                                                 63

<210> SEQ ID NO 13
<211> LENGTH: 63
<212> TYPE: DNA
```

<213> ORGANISM: Artificial Sequence
<220> FEATURE:
<223> OTHER INFORMATION: Primer

<400> SEQUENCE: 13
caagcagaag acggcatacg agataacgtg atagtcagtc agccacgcac ttgacttgtc      60
ttc                                                                   63

<210> SEQ ID NO 14
<211> LENGTH: 63
<212> TYPE: DNA
<213> ORGANISM: Artificial Sequence
<220> FEATURE:
<223> OTHER INFORMATION: Primer

<400> SEQUENCE: 14
caagcagaag acggcatacg agatcgctga tcagtcagtc agccacgcac ttgacttgtc      60
ttc                                                                   63

<210> SEQ ID NO 15
<211> LENGTH: 63
<212> TYPE: DNA
<213> ORGANISM: Artificial Sequence
<220> FEATURE:
<223> OTHER INFORMATION: Primer

<400> SEQUENCE: 15
caagcagaag acggcatacg agatcagatc tgagtcagtc agccacgcac ttgacttgtc      60
ttc                                                                   63

<210> SEQ ID NO 16
<211> LENGTH: 63
<212> TYPE: DNA
<213> ORGANISM: Artificial Sequence
<220> FEATURE:
<223> OTHER INFORMATION: Primer

<400> SEQUENCE: 16
caagcagaag acggcatacg agatatgcct aaagtcagtc agccacgcac ttgacttgtc      60
ttc                                                                   63

<210> SEQ ID NO 17
<211> LENGTH: 63
<212> TYPE: DNA
<213> ORGANISM: Artificial Sequence
<220> FEATURE:
<223> OTHER INFORMATION: Primer

<400> SEQUENCE: 17
caagcagaag acggcatacg agatagtaca agagtcagtc agccacgcac ttgacttgtc      60
ttc                                                                   63

<210> SEQ ID NO 18
<211> LENGTH: 63
<212> TYPE: DNA
<213> ORGANISM: Artificial Sequence
<220> FEATURE:
<223> OTHER INFORMATION: Primer

<400> SEQUENCE: 18
caagcagaag acggcatacg agatcatcaa gtagtcagtc agccacgcac ttgacttgtc      60
ttc                                                                   63

<210> SEQ ID NO 19
<211> LENGTH: 63
<212> TYPE: DNA
<213> ORGANISM: Artificial Sequence
<220> FEATURE:
<223> OTHER INFORMATION: Primer

<400> SEQUENCE: 19
caagcagaag acggcatacg agatagtggt caagtcagtc agccacgcac ttgacttgtc    60
ttc                                                                 63

<210> SEQ ID NO 20
<211> LENGTH: 63
<212> TYPE: DNA
<213> ORGANISM: Artificial Sequence
<220> FEATURE:
<223> OTHER INFORMATION: Primer

<400> SEQUENCE: 20
caagcagaag acggcatacg agataacaac caagtcagtc agccacgcac ttgacttgtc    60
ttc                                                                 63

<210> SEQ ID NO 21
<211> LENGTH: 63
<212> TYPE: DNA
<213> ORGANISM: Artificial Sequence
<220> FEATURE:
<223> OTHER INFORMATION: Primer

<400> SEQUENCE: 21
caagcagaag acggcatacg agatccgaag taagtcagtc agccacgcac ttgacttgtc    60
ttc                                                                 63

<210> SEQ ID NO 22
<211> LENGTH: 63
<212> TYPE: DNA
<213> ORGANISM: Artificial Sequence
<220> FEATURE:
<223> OTHER INFORMATION: Primer

<400> SEQUENCE: 22
caagcagaag acggcatacg agatccgtga gaagtcagtc agccacgcac ttgacttgtc    60
ttc                                                                 63

<210> SEQ ID NO 23
<211> LENGTH: 63
<212> TYPE: DNA
<213> ORGANISM: Artificial Sequence
<220> FEATURE:
<223> OTHER INFORMATION: Primer

<400> SEQUENCE: 23
caagcagaag acggcatacg agatcctcct gaagtcagtc agccacgcac ttgacttgtc    60
ttc                                                                 63

<210> SEQ ID NO 24
<211> LENGTH: 63
<212> TYPE: DNA
<213> ORGANISM: Artificial Sequence
<220> FEATURE:
<223> OTHER INFORMATION: Primer -continued

<400> SEQUENCE: 24
caagcagaag acggcatacg agatcgaact taagtcagtc agccacgcac ttgacttgtc    60
ttc                                                                 63

<210> SEQ ID NO 25
<211> LENGTH: 63
<212> TYPE: DNA
<213> ORGANISM: Artificial Sequence
<220> FEATURE:
<223> OTHER INFORMATION: Primer

<400> SEQUENCE: 25
caagcagaag acggcatacg agatcgactg gaagtcagtc agccacgcac ttgacttgtc    60
ttc                                                                 63

<210> SEQ ID NO 26
<211> LENGTH: 63
<212> TYPE: DNA
<213> ORGANISM: Artificial Sequence
<220> FEATURE:
<223> OTHER INFORMATION: Primer

<400> SEQUENCE: 26
caagcagaag acggcatacg agatcgcata caagtcagtc agccacgcac ttgacttgtc    60
ttc                                                                 63

<210> SEQ ID NO 27
<211> LENGTH: 63
<212> TYPE: DNA
<213> ORGANISM: Artificial Sequence
<220> FEATURE:
<223> OTHER INFORMATION: Primer

<400> SEQUENCE: 27
caagcagaag acggcatacg agatctcaat gaagtcagtc agccacgcac ttgacttgtc    60
ttc                                                                 63

<210> SEQ ID NO 28
<211> LENGTH: 63
<212> TYPE: DNA
<213> ORGANISM: Artificial Sequence
<220> FEATURE:
<223> OTHER INFORMATION: Primer

<400> SEQUENCE: 28
caagcagaag acggcatacg agatctgagc caagtcagtc agccacgcac ttgacttgtc    60
ttc                                                                 63

<210> SEQ ID NO 29
<211> LENGTH: 63
<212> TYPE: DNA
<213> ORGANISM: Artificial Sequence
<220> FEATURE:
<223> OTHER INFORMATION: Primer

<400> SEQUENCE: 29
caagcagaag acggcatacg agatctggca taagtcagtc agccacgcac ttgacttgtc    60
ttc                                                                 63

<210> SEQ ID NO 30
<211> LENGTH: 63

```
<212> TYPE: DNA
<213> ORGANISM: Artificial Sequence
<220> FEATURE:
<223> OTHER INFORMATION: Primer

<400> SEQUENCE: 30
caagcagaag acggcatacg agatgaatct gaagtcagtc agccacgcac ttgacttgtc      60
ttc                                                                   63

<210> SEQ ID NO 31
<211> LENGTH: 63
<212> TYPE: DNA
<213> ORGANISM: Artificial Sequence
<220> FEATURE:
<223> OTHER INFORMATION: Primer

<400> SEQUENCE: 31
caagcagaag acggcatacg agatgactag taagtcagtc agccacgcac ttgacttgtc      60
ttc                                                                   63

<210> SEQ ID NO 32
<211> LENGTH: 63
<212> TYPE: DNA
<213> ORGANISM: Artificial Sequence
<220> FEATURE:
<223> OTHER INFORMATION: Primer

<400> SEQUENCE: 32
caagcagaag acggcatacg agatgagctg aaagtcagtc agccacgcac ttgacttgtc      60
ttc                                                                   63

<210> SEQ ID NO 33
<211> LENGTH: 63
<212> TYPE: DNA
<213> ORGANISM: Artificial Sequence
<220> FEATURE:
<223> OTHER INFORMATION: Primer

<400> SEQUENCE: 33
caagcagaag acggcatacg agatgataga caagtcagtc agccacgcac ttgacttgtc      60
ttc                                                                   63

<210> SEQ ID NO 34
<211> LENGTH: 63
<212> TYPE: DNA
<213> ORGANISM: Artificial Sequence
<220> FEATURE:
<223> OTHER INFORMATION: Primer

<400> SEQUENCE: 34
caagcagaag acggcatacg agatgccaca taagtcagtc agccacgcac ttgacttgtc      60
ttc                                                                   63

<210> SEQ ID NO 35
<211> LENGTH: 63
<212> TYPE: DNA
<213> ORGANISM: Artificial Sequence
<220> FEATURE:
<223> OTHER INFORMATION: Primer

<400> SEQUENCE: 35
caagcagaag acggcatacg agatgcgagt aaagtcagtc agccacgcac ttgacttgtc      60
```

<210> SEQ ID NO 36
<211> LENGTH: 63
<212> TYPE: DNA
<213> ORGANISM: Artificial Sequence
<220> FEATURE:
<223> OTHER INFORMATION: Primer

<400> SEQUENCE: 36
caagcagaag acggcatacg agatgctaac gaagtcagtc agccacgcac ttgacttgtc    60
ttc    63

<210> SEQ ID NO 37
<211> LENGTH: 63
<212> TYPE: DNA
<213> ORGANISM: Artificial Sequence
<220> FEATURE:
<223> OTHER INFORMATION: Primer

<400> SEQUENCE: 37
caagcagaag acggcatacg agatgctcgg taagtcagtc agccacgcac ttgacttgtc    60
ttc    63

<210> SEQ ID NO 38
<211> LENGTH: 63
<212> TYPE: DNA
<213> ORGANISM: Artificial Sequence
<220> FEATURE:
<223> OTHER INFORMATION: Primer

<400> SEQUENCE: 38
caagcagaag acggcatacg agatggagaa caagtcagtc agccacgcac ttgacttgtc    60
ttc    63

<210> SEQ ID NO 39
<211> LENGTH: 63
<212> TYPE: DNA
<213> ORGANISM: Artificial Sequence
<220> FEATURE:
<223> OTHER INFORMATION: Primer

<400> SEQUENCE: 39
caagcagaag acggcatacg agatggtgcg aaagtcagtc agccacgcac ttgacttgtc    60
ttc    63

<210> SEQ ID NO 40
<211> LENGTH: 63
<212> TYPE: DNA
<213> ORGANISM: Artificial Sequence
<220> FEATURE:
<223> OTHER INFORMATION: Primer

<400> SEQUENCE: 40
caagcagaag acggcatacg agatgtacgc aaagtcagtc agccacgcac ttgacttgtc    60
ttc    63

<210> SEQ ID NO 41
<211> LENGTH: 63
<212> TYPE: DNA
<213> ORGANISM: Artificial Sequence
<220> FEATURE:
<223> OTHER INFORMATION: Primer

<400> SEQUENCE: 41
caagcagaag acggcatacg agatgtcgta gaagtcagtc agccacgcac ttgacttgtc    60
ttc    63

<210> SEQ ID NO 42
<211> LENGTH: 63
<212> TYPE: DNA
<213> ORGANISM: Artificial Sequence
<220> FEATURE:
<223> OTHER INFORMATION: Primer

<400> SEQUENCE: 42
caagcagaag acggcatacg agatgtctgt caagtcagtc agccacgcac ttgacttgtc    60
ttc    63

<210> SEQ ID NO 43
<211> LENGTH: 63
<212> TYPE: DNA
<213> ORGANISM: Artificial Sequence
<220> FEATURE:
<223> OTHER INFORMATION: Primer

<400> SEQUENCE: 43
caagcagaag acggcatacg agatacttga tgagtcagtc agccacgcac ttgacttgtc    60
ttc    63

<210> SEQ ID NO 44
<211> LENGTH: 63
<212> TYPE: DNA
<213> ORGANISM: Artificial Sequence
<220> FEATURE:
<223> OTHER INFORMATION: Primer

<400> SEQUENCE: 44
caagcagaag acggcatacg agattgacag acagtcagtc agccacgcac ttgacttgtc    60
ttc    63

<210> SEQ ID NO 45
<211> LENGTH: 40
<212> TYPE: DNA
<213> ORGANISM: Artificial Sequence
<220> FEATURE:
<223> OTHER INFORMATION: Primer

<400> SEQUENCE: 45
acccaactga atggagcggg tgctctatgc aatgttcgat    40

<210> SEQ ID NO 46
<211> LENGTH: 38
<212> TYPE: DNA
<213> ORGANISM: Artificial Sequence
<220> FEATURE:
<223> OTHER INFORMATION: Primer

<400> SEQUENCE: 46
acccaactga atggagccgt caccgcagat ccatgtac    38

<210> SEQ ID NO 47
<211> LENGTH: 36
<212> TYPE: DNA
<213> ORGANISM: Artificial Sequence
<220> FEATURE:

<223> OTHER INFORMATION: Primer

<400> SEQUENCE: 47
acccaactga atggagccga tcacaccgca gacgtt                              36

<210> SEQ ID NO 48
<211> LENGTH: 38
<212> TYPE: DNA
<213> ORGANISM: Artificial Sequence
<220> FEATURE:
<223> OTHER INFORMATION: Primer

<400> SEQUENCE: 48
acccaactga atggagccca tgaacgacgt cgaaacag                            38

<210> SEQ ID NO 49
<211> LENGTH: 35
<212> TYPE: DNA
<213> ORGANISM: Artificial Sequence
<220> FEATURE:
<223> OTHER INFORMATION: Primer

<400> SEQUENCE: 49
acccaactga atggagccct cgctgcccag aaagg                               35

<210> SEQ ID NO 50
<211> LENGTH: 40
<212> TYPE: DNA
<213> ORGANISM: Artificial Sequence
<220> FEATURE:
<223> OTHER INFORMATION: Primer

<400> SEQUENCE: 50
acccaactga atggagccta gtaatcgcag atcagcaacg                          40

<210> SEQ ID NO 51
<211> LENGTH: 39
<212> TYPE: DNA
<213> ORGANISM: Artificial Sequence
<220> FEATURE:
<223> OTHER INFORMATION: Primer

<400> SEQUENCE: 51
acgcacttga cttgtcttcg ggcttcggtg tacctcatc                           39

<210> SEQ ID NO 52
<211> LENGTH: 39
<212> TYPE: DNA
<213> ORGANISM: Artificial Sequence
<220> FEATURE:
<223> OTHER INFORMATION: Primer

<400> SEQUENCE: 52
acgcacttga cttgtcttcc gtcgctgatt ctcgcagtg                           39

<210> SEQ ID NO 53
<211> LENGTH: 38
<212> TYPE: DNA
<213> ORGANISM: Artificial Sequence
<220> FEATURE:
<223> OTHER INFORMATION: Primer

<400> SEQUENCE: 53
acgcacttga cttgtcttcg tttcgatcgg gcacatcc                            38

```
<210> SEQ ID NO 54
<211> LENGTH: 40
<212> TYPE: DNA
<213> ORGANISM: Artificial Sequence
<220> FEATURE:
<223> OTHER INFORMATION: Primer

<400> SEQUENCE: 54
acgcacttga cttgtcttcg ctcttcgtca gctcccactc                            40

<210> SEQ ID NO 55
<211> LENGTH: 40
<212> TYPE: DNA
<213> ORGANISM: Artificial Sequence
<220> FEATURE:
<223> OTHER INFORMATION: Primer

<400> SEQUENCE: 55
acgcacttga cttgtcttcg tcacattcga cgccaaacag                            40

<210> SEQ ID NO 56
<211> LENGTH: 37
<212> TYPE: DNA
<213> ORGANISM: Artificial Sequence
<220> FEATURE:
<223> OTHER INFORMATION: Primer

<400> SEQUENCE: 56
acgcacttga cttgtcttcg cctacgcccc accagtt                               37

<210> SEQ ID NO 57
<211> LENGTH: 45
<212> TYPE: DNA
<213> ORGANISM: Artificial Sequence
<220> FEATURE:
<223> OTHER INFORMATION: Primer

<400> SEQUENCE: 57
acgcacttga cttgtcttcc gcggacagca tcgattacgt gaatc                      45

<210> SEQ ID NO 58
<211> LENGTH: 48
<212> TYPE: DNA
<213> ORGANISM: Artificial Sequence
<220> FEATURE:
<223> OTHER INFORMATION: Primer

<400> SEQUENCE: 58
acccaactga atggagcgac ctgcagcagg tattcgacat tatcgttc                   48

<210> SEQ ID NO 59
<211> LENGTH: 44
<212> TYPE: DNA
<213> ORGANISM: Artificial Sequence
<220> FEATURE:
<223> OTHER INFORMATION: Primer

<400> SEQUENCE: 59
acgcacttga cttgtcttcc aacgggcgag tttgcaacgg aatc                       44

<210> SEQ ID NO 60
<211> LENGTH: 46
<212> TYPE: DNA
<213> ORGANISM: Artificial Sequence
<220> FEATURE:
<223> OTHER INFORMATION: Primer
```

<400> SEQUENCE: 60
acccaactga atggagcctg accgaacgat ggctggagat acatgc            46

<210> SEQ ID NO 61
<211> LENGTH: 44
<212> TYPE: DNA
<213> ORGANISM: Artificial Sequence
<220> FEATURE:
<223> OTHER INFORMATION: Primer

<400> SEQUENCE: 61
acgcacttga cttgtcttcc gaaataatt ttcggccggc gcac               44

<210> SEQ ID NO 62
<211> LENGTH: 41
<212> TYPE: DNA
<213> ORGANISM: Artificial Sequence
<220> FEATURE:
<223> OTHER INFORMATION: Primer

<400> SEQUENCE: 62
acgcacttga cttgtcttcg cgctgcccgt ttcaccactg g                 41

<210> SEQ ID NO 63
<211> LENGTH: 41
<212> TYPE: DNA
<213> ORGANISM: Artificial Sequence
<220> FEATURE:
<223> OTHER INFORMATION: Primer

<400> SEQUENCE: 63
acccaactga atggagcccg ccgaatccga tgctcaattt c                 41

<210> SEQ ID NO 64
<211> LENGTH: 45
<212> TYPE: DNA
<213> ORGANISM: Artificial Sequence
<220> FEATURE:
<223> OTHER INFORMATION: Primer

<400> SEQUENCE: 64
acgcacttga cttgtcttca gcttcgcata cagcacttcc gccag             45

<210> SEQ ID NO 65
<211> LENGTH: 40
<212> TYPE: DNA
<213> ORGANISM: Artificial Sequence
<220> FEATURE:
<223> OTHER INFORMATION: Primer

<400> SEQUENCE: 65
acccaactga atggagcgcc ggcttggctt cgtccttgtc                   40

<210> SEQ ID NO 66
<211> LENGTH: 45
<212> TYPE: DNA
<213> ORGANISM: Artificial Sequence
<220> FEATURE:
<223> OTHER INFORMATION: Primer

<400> SEQUENCE: 66
acgcacttga cttgtcttcc aaatgggaag cgagctccct tccga             45

<210> SEQ ID NO 67
<211> LENGTH: 44

```
<212> TYPE: DNA
<213> ORGANISM: Artificial Sequence
<220> FEATURE:
<223> OTHER INFORMATION: Primer

<400> SEQUENCE: 67
acccaactga atggagccga caggcatcgg gcgactacta ccag          44

<210> SEQ ID NO 68
<211> LENGTH: 42
<212> TYPE: DNA
<213> ORGANISM: Artificial Sequence
<220> FEATURE:
<223> OTHER INFORMATION: Primer

<400> SEQUENCE: 68
acccaactga atggagccgt gacgccgtcg ggaaagatca tc            42

<210> SEQ ID NO 69
<211> LENGTH: 43
<212> TYPE: DNA
<213> ORGANISM: Artificial Sequence
<220> FEATURE:
<223> OTHER INFORMATION: Primer

<400> SEQUENCE: 69
acccaactga atggagcggg cggacgaaaa cccttgagca cag           43

<210> SEQ ID NO 70
<211> LENGTH: 45
<212> TYPE: DNA
<213> ORGANISM: Artificial Sequence
<220> FEATURE:
<223> OTHER INFORMATION: Primer

<400> SEQUENCE: 70
acccaactga atggagcgcg gcagccgttg aggcaaaagt gatac         45

<210> SEQ ID NO 71
<211> LENGTH: 47
<212> TYPE: DNA
<213> ORGANISM: Artificial Sequence
<220> FEATURE:
<223> OTHER INFORMATION: Primer

<400> SEQUENCE: 71
acgcacttga cttgtcttcg ccgggatgcc ttacctagac gcaatga       47

<210> SEQ ID NO 72
<211> LENGTH: 48
<212> TYPE: DNA
<213> ORGANISM: Artificial Sequence
<220> FEATURE:
<223> OTHER INFORMATION: Primer

<400> SEQUENCE: 72
acgcacttga cttgtcttcc gagttccgtc cggttaagcg tgacagtc      48
```

SYSTEMS AND METHODS FOR UNIVERSAL TAIL-BASED INDEXING STRATEGIES FOR AMPLICON SEQUENCING

CROSS-REFERENCE TO RELATED APPLICATIONS

The present application is the U.S. National Stage of International Application No. PCT/US2014/064890, filed Nov. 10, 2014, which claims priority to U.S. Patent Application No. 61/902,432 filed Nov. 11, 2013, the contents of each of which are hereby incorporated by reference in their entireties.

REFERENCE TO SEQUENCE LISTING SUBMITTED ELECTRONICALLY

The official copy of the sequence listing is submitted electronically via EFS-Web as an ASCII-formatted sequence listing with a file named "91482_154_Sequence_Listing.txt" created on Nov. 5, 2014, and having a size of 16 kilobytes, and is filed concurrently with the specification. The sequence listing contained in this ASCII-formatted document is part of the specification and is herein incorporated by reference in its entirety.

FIELD OF THE INVENTION

This application relates to systems and methods that can be used in conjunction with sequencing processes, and more particularly, this application relates to systems and methods of preparing amplicon products for sequencing through the use of a universal tail-based indexing strategy.

BACKGROUND OF THE INVENTION

High throughput amplicon sequencing of genomic regions of interest can be very useful for a variety of molecular genetic genotyping applications, including forensic and clinical sample analysis. Some conventional sequencing platforms provide for rapid, high yield sequence data, which can enable the sequencing of multiple amplicons from many samples in a short period of time. However, efficient use of at least some of these sequencing platforms requires the use of sample barcoding, which can be cumbersome and expensive when dealing with tens to thousands of samples. This complication is further compounded if multiple amplicons are to be sequenced from each sample. As such, there is a demonstrated need to develop systems and methods that enable the production of sequencing platform-ready amplicons in a multiplex fashion with a common set of indexing oligonucleotide sequences that can be used in preparing any amplicon for sequencing.

For example, PCR reactions can be used to generate amplicons that are sequencing-platform ready for some systems (e.g., bacterial ribosomal gene sequencing) (J G Caporaso et al. (2012) ISME J. 6(8) 1621-1624). Moreover, some conventional methodologies include indexing, which comprises the use of a plasmid for production of the indexing oligonucleotide (Chubiz et al. (2012) PLoS One 7(10) e47959). Other conventional sequencing platforms may be compatible with custom amplicon sequencing products designed for different eukaryotic organisms, but these conventional systems utilize an initial hybridization of probes with an extension-ligation reaction followed by a PCR reaction requiring at least 50 nanograms (ng) of pure, high quality DNA template as starting material. As such, there is a demonstrated need for systems and methods that provide for substantially or completely simultaneous amplification of multiple amplicon targets from any organism in a PCR reaction with subsequent universal indexing addition that requires only a single set of common indexing oligonucleotides that can be used with any set of amplicons from any type of nucleic acid-based sample, regardless of the quality of the sample.

SUMMARY

Some embodiments of the invention include a method of preparing a sample for sequencing that includes receiving a sample and amplifying at least one marker within the sample. In some embodiments, amplification of the first maker may include mixing the sample with a first oligonucleotide that comprises a first universal tail sequence and a second oligonucleotide that comprises a second universal tail sequence. In some aspects of the invention, the first universal tail sequence and the second universal tail sequence are different sequences. In some embodiments of the invention, the sequences of the first and second universal tail sequences may be at least partially correlated with the guanine-cytosine content of the first marker, and the organism from which the first marker is to be amplified.

In some aspects, the method may further include amplifying a second marker by mixing the sample with a third oligonucleotide that includes the first universal tail sequence and a fourth oligonucleotide that includes the second universal tail sequence. For example, the first marker and the second marker can be amplified in the same reaction vessel such that the amplification of these two markers occurs during a multiplex PCR assay. In some embodiments, more than two markers can be amplified during the multiplex PCR assay.

In addition, the amplification of the first marker and the second marker can result in the production of a first amplicon and the second amplicon that comprise the first and second universal tail sequences integrated therein. Some embodiments of the invention further include adding an index to the first amplicon and the second amplicon using at least one indexing oligonucleotide. For example, the indexing oligonucleotide comprises a complementary sequence that recognizes at least one of the first universal tail sequence and the second universal tail sequence that has been previously integrated within the first and second amplicons.

In some aspects of the invention, the sample can be from any source desirable for sequencing analysis. For example, the sample can be a portion of a pathogenic organism and the first and/or second markers may be antibiotic resistance genes. In other embodiments, the sample may be from a castor bean or a castor bean product. Moreover, the sample may also be from an animal, such as a human. In some aspects, the sample may be from a human and the marker may be affiliated with a known human condition, such as cystic fibrosis.

In certain aspects, the first universal tail sequence and the second universal tail sequence independently comprise a sequence selected from the group consisting of SEQ ID NO: 1, SEQ ID NO: 2, SEQ ID NO: 3, and SEQ ID NO: 4.

In other aspects, the at least one indexing oligonucleotide comprises a sequence selected from the group consisting of SEQ ID NOs: 9-44.

Some embodiments of the invention provide a method of assessing the presence of at least one antibiotic resistance gene within a population of organisms. The method may include initially receiving a sample of the population of organisms and then extracting a template from the sample. Moreover, the method may also include performing a multiplex polymerase chain reaction assay that includes amplifying a first marker from the template and a second marker from the template within the same reaction vessel.

In yet other embodiments, the sequencing comprises amplifying the first marker and/or second marker with a sequencing primer. The sequencing primer may comprise a sequence selected from the group consisting of SEQ ID NO: 6, SEQ ID NO: 7, and SEQ ID NO: 8.

In some aspects, amplifying the first marker can include mixing the template with a first oligonucleotide that includes a first universal tail sequence and a second oligonucleotide that includes a second universal tail sequence. Similarly, amplifying the second marker includes mixing the template with a third oligonucleotide comprising the first universal tail sequence and a fourth oligonucleotide comprising the second universal tail sequence. As a result of this amplification step, a first amplicon and a second amplicon are produced. In other embodiments, more than a first amplicon and a second amplicon can be produced.

In some aspects, the template can be any variety of molecules. For example, the template can be a crude nucleic acid extract from the population of organisms that may include DNA and/or RNA. In some aspects, the template can comprise double-stranded or single-stranded DNA. Moreover, in some embodiments, the template can comprise RNA.

In other embodiments, the present invention is directed to a method of determining gene copy number and/or quantifying gene expression in a sample, the method comprising the steps of: a) receiving a sample; b) amplifying at least a first marker within the sample to produce a first amplicon, wherein amplifying at least the first marker comprises mixing the sample with a first oligonucleotide comprising a first universal tail sequence and a second oligonucleotide comprising a second universal tail sequence, wherein the first universal tail sequence and the second oligonucleotide sequence are different; c) adding an index to the first amplicon using at least one indexing oligonucleotide, wherein the at least one indexing oligonucleotide comprises a complementary sequence that recognizes at least one of the first universal tail sequence and the second universal tail sequence; d) sequencing the first amplicon to produce a number of sequencing reads; and e) determining gene copy number and/or quantifying gene expression from differential target sequencing read counts wherein the sequencing read counts of the sample are compared with sequencing read counts of a reference sample.

In certain aspects, the reference sample is a sample from a wild-type organism. In other aspects, the reference sample is an internal standard comprising one or more markers of interest. In yet other aspects, the reference sample is derived from a healthy subject or from a healthy tissue in which disease has not been detected.

Additional objectives, advantages and novel features will be set forth in the description which follows or will become apparent to those skilled in the art upon examination of the drawings and detailed description which follows.

BRIEF DESCRIPTION OF THE DRAWINGS

FIG. 1 is a simplified illustration detailing steps that can be performed in accord with some embodiments of the invention.

FIG. 2 is a listing of universal tail sequences and oligonucleotide sequences that can be used in conjunction with the universal tail sequences.

FIG. 6 shows the potential of the UT amplicon multiplex assays for quantitative analysis.

Figure 1A:
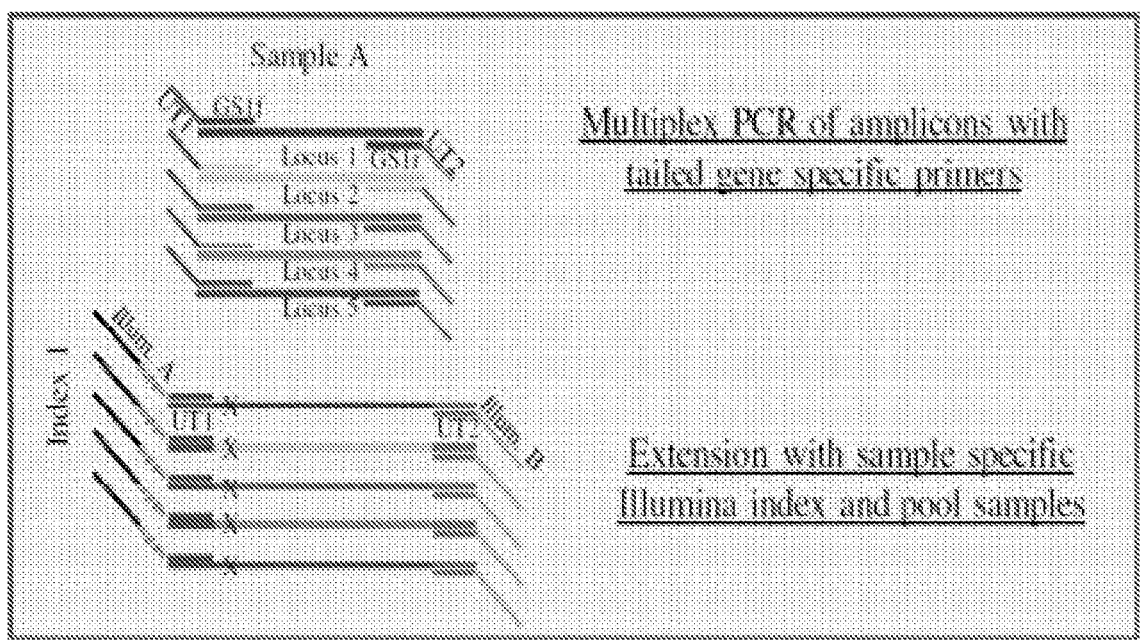
FIG. 1A depicts multiplex PCR of amplicons with tailed gene specific primers.

The headings used in the figures should not be interpreted to limit the scope of the claims.

DETAILED DESCRIPTION

Some embodiments of the invention include systems and methods of preparing samples for one or more downstream processes that can be used for assessing one or more markers. Some embodiments of the invention may comprise a universal indexing sequencing strategy for use in downstream sequencing platform processes. By way of example only, some embodiments of the invention comprise a universal indexing sequencing strategy that can be used to amplify multiple genomic regions (e.g., markers, as described below) from a DNA sample simultaneously in a single reaction for the sequencing of one or more amplicons. One or more embodiments of the invention can be used with any desired sequencing platform, such as the ILLUMINA® Next Generation Sequencing (e.g., MiSEQ) platform, Life Technologies' Ion Torrent System, or any other sequencing system now known or developed in the future.

Moreover, some embodiments of the invention can be configured to be used with non-DNA samples (e.g., RNA samples) for applications that may comprise functionalities such as quantification of expression of one or more markers. For example, RNA can be extracted from a sample, converted to cDNA using techniques known in the art, and the cDNA can function as the template for additional processes (e.g., multiplex polymerase chain reaction assays and subsequent sequencing).

Some embodiments may be configured to enable relatively simple, inexpensive, and efficient preparation of samples for use on, in, and/or with downstream sequencing platforms. For example, this improvement over some conventional systems can originate from the use of a sequence coupled to one or more oligonucleotides/primers (as used herein, oligonucleotides and primers are used interchangeably). More specifically, one or more amplicons per sample can be generated using a hybrid oligonucleotide that is designed for amplification of a marker and incorporation of at least one universal tail sequence into the resulting amplicon. As a result, additional steps that may be conventionally required to prepare samples for sequencing can be limited or removed entirely.

In addition, at least some embodiments of the invention comprise the use of PCR before sequencing such that only limited amounts of starting material are necessary and the starting material need not be of high quality (e.g., genomic DNA, crude DNA extracts, single stranded DNA, RNA, cDNA, etc.). In contrast, many conventional sample preparation systems may require relatively large amounts of starting material of relatively high quality, which can limit the use of these systems.

Some embodiments of the invention can be used for and/or in complement with high-throughput amplicon sequencing of markers, which can be very useful for a variety of molecular genetic genotyping applications, including forensic and clinical sample analysis. For example, use of the systems and methods of the invention can be employed with sequencing platforms to provide rapid, high-yield sequence data, which can enable the sequencing of multiple markers/amplicons from many samples in a relatively short period of time. In particular, many sequencing platforms may require the use of sample barcoding, which can be cumbersome and expensive when dealing with tens to hundreds or thousands of samples, which is a difficulty that can be further compounded if multiple amplicons are to be sequenced from each sample. As such, some embodiments of the invention can include systems and methods that comprise the use of universal tail sequences that can enable the production of sequencing platform-ready amplicons in a multiplex fashion. As described in greater detail below, one or more sets of indexing oligonucleotide sequences can in connection with amplicons that have one or more universal tail sequences incorporated therein.

Generally, some embodiments of the present invention can be used to detect, identify, assess, sequence, or otherwise evaluate a marker. A marker may be any molecular structure produced by a cell, expressed inside the cell, accessible on the cell surface, or secreted by the cell. A marker may be any protein, carbohydrate, fatty acid, nucleic acid, catalytic site, or any combination of these such as an enzyme, glycoprotein, cell membrane, virus, a particular cell, or other uni- or multimolecular structure. A marker may be represented by a sequence of a nucleic acid or any other molecules derived from the nucleic acid. Examples of such nucleic acids include miRNA, tRNA, siRNA, mRNA, cDNA, genomic DNA sequences, single-stranded DNA, or complementary sequences thereof. Alternatively, a marker may be represented by a protein sequence. The concept of a marker is not limited to the exact nucleic acid sequence or protein sequence or products thereof, rather it encompasses all molecules that may be detected by a method of assessing the marker. Without being limited by the theory, the detection, identification, assessment, sequencing, or any other evaluation of the marker may encompass an assessment of a change in copy number (e.g., copy number of a gene or other forms of nucleic acid) or in the detection of one or more translocations. Moreover, in some embodiments, the marker may be relevant to a particular phenotype or genotype. By way of example only, in some embodiments, the marker may be related to phenotypes including antibiotic resistance, virulence, or any other phenotype.

Therefore, examples of molecules encompassed by a marker represented by a particular sequence further include alleles of the gene used as a marker. An allele includes any form of a particular nucleic acid that may be recognized as a form of the particular nucleic acid on account of its location, sequence, or any other characteristic that may identify it as being a form of the particular gene. Alleles include but need not be limited to forms of a gene that include point mutations, silent mutations, deletions, frameshift mutations, single nucleotide polymorphisms (SNPs), inversions, translocations, heterochromatic insertions, and differentially methylated sequences relative to a reference gene, whether one or in combination. An allele of a gene may or may not produce a functional protein; may produce a protein with altered function, localization, stability, dimerization, or protein-protein interaction; may have overexpression, underexpression or no expression; may have altered temporal or spatial expression specificity; or may have altered copy number (e.g., greater or less numbers of copies of the allele). An allele may also be called a mutation or a mutant. An allele may be compared to another allele that may be termed a wild type form of an allele. In some cases, the wild type allele is more common than the mutant.

Some embodiments of the invention may comprise the use of one or more methods of amplifying a nucleic acid-based starting material (i.e., a template, including genomic DNA, crude DNA extract, single-stranded DNA, double-stranded DNA, cDNA, RNA, or any other single-stranded or double-stranded nucleic acids). Nucleic acids may be selectively and specifically amplified from a template nucleic acid contained in a sample. In some nucleic acid amplification methods, the copies are generated exponentially. Examples of nucleic acid amplification methods known in the art include: polymerase chain reaction (PCR), ligase chain reaction (LCR), self-sustained sequence replication (3SR), nucleic acid sequence based amplification (NASBA), strand displacement amplification (SDA), amplification with Qβ replicase, whole genome amplification with enzymes such as φ29, whole genome PCR, in vitro transcription with T7 RNA polymerase or any other RNA polymerase, or any other method by which copies of a desired sequence are generated.

In addition to genomic DNA, any polynucleotide sequence can be amplified with an appropriate set of primer molecules. In particular, the amplified segments created by the PCR process itself are, themselves, efficient templates for subsequent PCR amplifications.

PCR generally involves the mixing of a nucleic acid sample, two or more primers or oligonucleotides (primers and oligonucleotides are used interchangeably herein) that are designed to recognize the template DNA, a DNA polymerase, which may be a thermostable DNA polymerase such as Taq or Pfu, and deoxyribose nucleoside triphosphates (dNTP's). In some embodiments, the DNA polymerase used can comprise a high fidelity Taq polymerase such that the error rate of incorrect incorporation of dNTPs is less than one per 1,000 base pairs. Reverse transcription PCR, quantitative reverse transcription PCR, and quantitative real time reverse transcription PCR are other specific examples of PCR. In general, the reaction mixture is subjected to temperature cycles comprising a denaturation stage (typically 80-100° C.), an annealing stage with a temperature that is selected based on the melting temperature (Tm) of the primers and the degeneracy of the primers, and an extension stage (for example 40-75° C.). In real-time PCR analysis, additional reagents, methods, optical detection systems, and devices known in the art are used that allow a measurement of the magnitude of fluorescence in proportion to concentration of amplified template. In such analyses, incorporation of fluorescent dye into the amplified strands may be detected or measured.

Either primers or primers along with probes allow a quantification of the amount of specific template DNA present in the initial sample. In addition, RNA may be detected by PCR analysis by first creating a DNA template from RNA through a reverse transcriptase enzyme (i.e., the creation of cDNA). The marker expression may be detected by quantitative PCR analysis facilitating genotyping analysis of the samples.

"Amplification" is a special case of nucleic acid replication involving template specificity. Amplification may be a template-specific replication or a non-template-specific replication (i.e., replication may be specific template-dependent or not). Template specificity is here distinguished from fidelity of replication (synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out. The amplification process may result in the production of one or more amplicons.

The term "template" refers to nucleic acid originating from a sample that is analyzed for the presence of one or more markers. In contrast, "background template" or "control" is used in reference to nucleic acid other than sample template that may or may not be present in a sample. Background template is most often inadvertent. It may be the result of carryover, or it may be due to the presence of nucleic acid contaminants sought to be purified out of the sample. For example, nucleic acids from organisms other than those to be detected may be present as background in a test sample.

In addition to primers and probes, template specificity is also achieved in some amplification techniques by the choice of enzyme. Amplification enzymes are enzymes that, under the conditions in which they are used, will process only specific sequences of nucleic acid in a heterogeneous mixture of nucleic acid. Other nucleic acid sequences will not be replicated by this amplification enzyme. Similarly, in the case of T7 RNA polymerase, this amplification enzyme has a stringent specificity for its own promoters (Chamberlin et al. (1970) Nature (228):227). In the case of T4 DNA ligase, the enzyme will not ligate the two oligonucleotides or polynucleotides, where there is a mismatch between the oligonucleotide or polynucleotide substrate and the template at the ligation junction (Wu and Wallace (1989) Genomics (4):560). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.) (1989) PCR Technology, Stockton Press).

The term "amplifiable nucleic acid" refers to nucleic acids that may be amplified by any amplification method. It is contemplated that "amplifiable nucleic acid" will usually comprise "sample template." The terms "PCR product," "PCR fragment," "amplification product," and "amplicon" refer to the resultant mixture of compounds after two or more cycles of the PCR steps of denaturation, annealing and extension. These terms encompass the case where there has been amplification of one or more segments of one or more target sequences.

In some forms of PCR assays, quantification of a target in an unknown sample is often required. Such quantification may be determined in reference to the quantity of a control sample. The control sample starting material/template may be co-amplified in the same tube in a multiplex assay or may be amplified in a separate tube. Generally, the control sample contains template at a known concentration. The control sample template may be a plasmid construct comprising only one copy of the amplification region to be used as quantification reference. To calculate the quantity of a target in an unknown sample, various mathematical models are established. Calculations are based on the comparison of the distinct cycle determined by various methods, e.g., crossing points (CP) and cycle threshold values (Ct) at a constant level of fluorescence; or CP acquisition according to established mathematic algorithm.

Some embodiments of the invention may comprise a multiplex assay. As used herein, the term "multiplex" refers to the production of more than one amplicon, FOR product, FOR fragment, amplification product, etc. in a single reaction vessel. In other words, multiplex is to be construed as the amplification of more than one target-specific sequences within a PCR reaction or assay within the same PCR assay mixture (e.g., more than one amplicon is produced within a single vessel that contains all of the reagents necessary to perform a PCR reaction). In some embodiments, a step prior to performing the FOR (or RT-PCR, quantitative RT-PCR, etc.) reaction can occur such that sets of primers and/or primers and probes are designed, produced, and optimized within a given set of reaction conditions to ensure proper amplicon production during the performance of the FOR.

The algorithm for Ct values in real time-PCR calculates the cycle at which each FOR amplification reaches a significant threshold. The calculated Ct value is proportional to the number of marker copies present in the sample, and the Ct value is a precise quantitative measurement of the copies of the marker found in any sample. In other words, Ct values represent the presence of respective marker that the primer sets are designed to recognize. If the marker is missing in a sample, there should be no amplification in the Real Time-PCR reaction.

Alternatively, the Cp value may be utilized. A Cp value represents the cycle at which the increase of fluorescence is highest and where the logarithmic phase of a PCR begins. The LightCycler® 480 Software calculates the second derivatives of entire amplification curves and determines where this value is at its maximum. By using the second-derivative algorithm, data obtained are more reliable and reproducible, even if fluorescence is relatively low.

The various and non-limiting embodiments of the PCR-based method detecting marker expression level as described herein may comprise one or more probes and/or primers. Generally, the probe or primer contains a sequence complementary to a sequence specific to a region of the nucleic acid of the marker gene. A sequence having less than 60% 70%, 80%, 90%, 95%, 99% or 100% identity to the identified gene sequence may also be used for probe or primer design if it is capable of binding to its complementary sequence of the desired target sequence in marker nucleic acid.

Some embodiments of the invention may include a method of comparing a marker in a sample relative to one or more control samples. A control may be any sample with a previously determined level of expression. A control may comprise material within the sample or material from sources other than the sample. Alternatively, the expression of a marker in a sample may be compared to a control that has a level of expression predetermined to signal or not signal a cellular or physiological characteristic. This level of expression may be derived from a single source of material including the sample itself or from a set of sources.

The sample in this method is preferably a biological sample from a subject. The term "sample" or "biological sample" is used in its broadest sense. Depending upon the embodiment of the invention, for example, a sample may comprise a bodily fluid including whole blood, serum, plasma, urine, saliva, cerebral spinal fluid, semen, vaginal fluid, pulmonary fluid, tears, perspiration, mucus and the like; an extract from a cell, chromosome, organelle, or membrane isolated from a cell; a cell; genomic DNA, RNA, or cDNA, in solution or bound to a substrate; a tissue; a tissue print, or any other material isolated in whole or in part from a living subject or organism. Biological samples may also include sections of tissues such as biopsy and autopsy samples, and frozen sections taken for histologic purposes such as blood, plasma, serum, sputum, stool, tears, mucus, hair, skin, and the like. Biological samples also include explants and primary and/or transformed cell cultures derived from patient tissues. In some embodiments, sample may comprise a portion of a non-animal organism, such as a plant (e.g., castor beans or derivatives thereof).

In some embodiments, sample or biological sample may include a bodily tissue, fluid, or any other specimen that may be obtained from a living organism that may comprise additional living organisms. By way of example only, in some embodiments, sample or biological sample may include a specimen from a first organism (e.g., a human) that may further comprise an additional organism (e.g., bacteria, including pathogenic or non-pathogenic/commensal bacteria, viruses, parasites, fungi, including pathogenic or non-pathogenic fungi, etc.). In some embodiments of the invention, the additional organism may be separately cultured after isolation of the sample to provide additional starting materials for downstream analyses. In some embodiments, the sample or biological sample may comprise a direct portion of the additional, non-human organism and the host organism (e.g., a biopsy or sputum sample that contains human cells and bacteria).

The invention may further comprise the step of sequencing the amplicon. Methods of sequencing include but need not be limited to any form of DNA sequencing including Sanger, next-generation sequencing, pyrosequencing, SOLiD sequencing, massively parallel sequencing, pooled, and barcoded DNA sequencing or any other sequencing method now known or yet to be disclosed.

In Sanger Sequencing, a single-stranded DNA template, a primer, a DNA polymerase, nucleotides and a label such as a radioactive label conjugated with the nucleotide base or a fluorescent label conjugated to the primer, and one chain terminator base comprising a dideoxynucleotide (ddATP, ddGTP, ddCTP, or ddTTP, are added to each of four reaction (one reaction for each of the chain terminator bases). The sequence may be determined by electrophoresis of the resulting strands. In dye terminator sequencing, each of the chain termination bases is labeled with a fluorescent label of a different wavelength that allows the sequencing to be performed in a single reaction.

In pyrosequencing, the addition of a base to a single-stranded template to be sequenced by a polymerase results in the release of a pyrophosphate upon nucleotide incorporation. An ATP sulfurylase enzyme converts pyrophosphate into ATP that in turn catalyzes the conversion of luciferin to oxyluciferin which results in the generation of visible light that is then detected by a camera or other sensor capable of capturing visible light.

In SOLiD sequencing, the molecule to be sequenced is fragmented and used to prepare a population of clonal magnetic beads (in which each bead is conjugated to a plurality of copies of a single fragment) with an adaptor sequence and alternatively a barcode sequence. The beads are bound to a glass surface. Sequencing is then performed through 2-base encoding.

In massively parallel sequencing, randomly fragmented targeted nucleic acids and/or amplicons are attached to a surface. The fragments/amplicons are extended and bridge amplified to create a flow cell with clusters, each with a plurality of copies of a single fragment sequence. The templates are sequenced by synthesizing the fragments in parallel. Bases are indicated by the release of a fluorescent dye correlating to the addition of the particular base to the fragment. Nucleic acid sequences may be identified by the IUAPC letter code which is as follows: A—Adenine base; C—Cytosine base; G—guanine base; T or U—thymine or uracil base. M-A or C; R-A or G; W-A or T; S-C or G; Y-C or T; K-G or T; V-A or C or G; H-A or C or T; D-A or G or T; B C or G or T; N or X-A or C or G or T. Note that T or U may be used interchangeably depending on whether the nucleic acid is DNA or RNA. A sequence having less than 60%, 70%, 80%, 90%, 95%, 99% or 100% identity to the identifying sequence may still be encompassed by the invention if it is able of binding to its complimentary sequence and/or facilitating nucleic acid amplification of a desired target sequence. In some embodiments, as previously mentioned, the method may include the use of massively parallel sequencing, as detailed in U.S. Pat. Nos. 8,431,348 and 7,754,429, which are hereby incorporated by reference in their entirety.

Some embodiments of the invention comprise multiple steps and/or processes that are carried out to execute the universal tail indexing strategy to prepare amplicons for sequencing. In some embodiments, one or more makers for a given sample or template can be selected. Some embodiments of the invention can be used in conjunction with an analysis of one or more markers (e.g., genes/alleles) associated with a particular phenotype (e.g., resistance to one or more pharmaceuticals, such as antibiotics). By way of example only, some embodiments of the invention can be used to detect and/or quantify the development of antibiotic resistance in populations of patients infected with an organism (e.g., *Mycobacterium tuberculosis*). As such, in some aspects, prior to performing additional steps, an investigator can assess the markers present within the genome of the organism to determine which markers are implicated in the development of antibiotic resistance. For example, markers can be selected that may contain a SNP or other change or alteration that can confer at least partial antibiotic resistance. In other aspects of the invention, markers can be selected that are not implicated in antibiotic resistance, but are associated with other phenotypes/genotypes that are desirable for further analysis. Regardless of the markers selected (e.g., markers related to antibiotic resistance or markers that are not related to antibiotic resistance), the markers may comprise sequence variations that comprise a degree of differentiality relative to a wild-type or control version of the marker such that a comparison of the marker and the wild-type/control sequence of the marker will enable an investigator to assess the genotype of the organism being tested.

After selection of the markers, marker-specific primers/oligonucleotides can be designed for the amplification of the markers to produce the desired amplicons. As is known in the art, a forward and a reverse marker-specific primer can be designed to amplify the marker from a nucleic acid sample. In some embodiments, the forward and reverse primers can be designed to produce an amplicon (e.g., some or all of the sequence of the marker) of a desired length. For example, the length of the amplicon may comprise approximately 50 base pairs (bp), 100 bp, 150 bp, 200 bp, 250 bp, 300 bp, 350 bp, 400 bp, 450 bp, 500 bp, 1,000 bp, or any size amplicon therebetween.

As previously mentioned, some embodiments of the invention may include a multiplex PCR reaction. For example, marker-specific primers can be designed for multiple markers or multiple regions of the same marker such that multiple amplicons of between about 50 bp and 1,000 bp are being produced within a single FOR reaction vessel. In other words, the forward and reverse primers can be designed to function within a given set of temperature parameters such that more than one amplicon can be successfully amplified from a given template within a single PCR reaction mixture. As such, multiple amplicons can be prepared using the universal tail indexing strategy for sequencing preparation. In some embodiments, the multiplex FOR reaction can result in the production of between two and 10 amplicons. In other embodiments, the multiplex PCR reaction can result in the production of more than 10 amplicons. In some embodiments, the multiplex PCR reaction can be optimized to produce about five amplicons.

In some embodiments, the forward and reverse pruners that have been designed for each of the markers can be modified to include a universal tail. For example, the universal tail sequences can be relatively or completely unique sequences of nucleotides that are coupled to the 5' ends of some or all of the forward and reverse marker-specific primers. In some aspects, the universal tail sequences can be selected such that there is little to no overlap in sequence between portions of the markers that are being amplified and the universal tail sequences. Moreover, the universal tail sequences can comprise a length between ten and twenty nucleotides in length. In some embodiments, the universal tail sequences can be any other length, as desired by the user to meet the needs and requirements of the reaction. As such, the universal tail sequences can exhibit a relatively negligible impact on binding of the forward and reverse marker-specific primers to the template sequence to enable amplification. Moreover, as a result of being included on the 5' end of the forward and reverse marker-specific primers, the universal tail sequences will form a portion of the resulting amplicons. In addition, in some aspects of the invention, the sequences selected for the universal tail sequences can be at least partially correlated with the chemical composition of the template nucleic acids. For example, in some aspects, the sequences selected for the universal tail sequences can be at least partially correlated with the G-C content of the organism from which the template is isolated.

In some aspects, some or all of the universal tail sequences can be at least partially unique. In some embodiments, each of the 5' ends of all of the forward marker-specific primers within a given PCR assay mixture can comprise the same or a similar universal tail sequence (e.g., a first universal tail sequence or UT1). Similarly, each of the 5' ends of all of the reverse marker-specific primers within the same PCR assay mixture can comprise a second universal tail sequence (UT2) that differs from the first universal tail sequence. As such, each respective sample from which a template sequence is used in the multiplex PCR assay will have two unique universal tail sequences. Accordingly, each forward and reverse marker-specific primer within a multiplex PCR mixture will include a unique universal tail sequence. For example, if the PCR includes 35 different samples, 35 universal tail sequences can be employed for the forward primers in each of the 35 unique reactions (i.e., not including technical replicates) and 35 universal tail sequences can be employed for the reverse primers in each of the 35 unique reactions (i.e., not including technical replicates). Overall, the forward and reverse marker-specific primers that each comprise the universal tail sequences can comprise a generally short length (e.g., 25-50 bp), which can facilitate simultaneous amplification of multiple targets in a single reaction.

In addition, some embodiments of the invention may comprise performing quantitative FOR to optimize the multiplex PCR assay. For example, after design of the forward and reverse marker-specific primers that each include a universal tail sequence, the contemplated multiplex PCR assays can be performed using quantitative FOR (e.g., using DNA as a template) to assess relative quantities of the amplicons produced. Accordingly, the sequence coverage of each amplicon is considered to be equal if the quantities of the amplicons produced by the multiplex quantitative FOR appear to be equal. If the quantities of the amplicons produced by the multiplex quantitative FOR do not appear to be equal, the forward and/or reverse marker-specific primers can be altered and re-optimized until adequate quantities of amplicons are produced.

After design and adequate optimization of the multiplex PCR assay comprising multiple forward and reverse marker-specific primers that each include universal tail sequences, the multiplex PCR can be performed to obtain the amplicons. In some embodiments, template that has been previously isolated from a sample can be used for the amplification of the amplicons. In some aspects, multiple PCR reaction replicates can be performed for each sample template and one or more control templates. For example, in embodiments configured to assess/quantify the development of antibiotic resistance in a population of organisms (e.g., bacteria), DNA can be isolated from one or more representative members of the population (e.g., colonies) to serve as the template. Moreover, DNA may also be isolated from a population of similar organisms that are known to not have a genotype that confers some level of antibiotic resistance to function as a control (e.g., a negative control). In addition, DNA may also be isolated from a population of similar organisms that are known to have a genotype that confers some level of antibiotic resistance to function as a control (e.g., a positive control). In other embodiments, the markers associated with a particular phenotype (e.g., antibiotic resistance) may already be known such that one or both of the control samples may not be necessary for comparison.

In certain aspects, the presence of antibiotic resistance in a population of organisms is indicated by detection of a particular gene or allele in the population. Non-limiting examples of genes that confer antibiotic resistance include $bla_{tem}$, $bla_{shv}$, $bla_{rob}$, $bla_{oxa}$, blaZ, aadB, aacC1, aacC2, aacC3, aac6'-IIa, aacA4, aad(6'), vanA, vanB, vanC, msrA, sarA, aac(6') aph(2"), vat, vga, ermA, ermB, ermC, mecA, int, sul, mecA, aac2ia, aac2ib, aac2ic, aac2id, aac2i, aac3ia, aac3iia, aac3iib, aac3iii, aac3iv, aac3ix, aac3vi, aac3viii, aac3vii, aac3x, aac6i, aac6ia, aac6ib, aac6ic, aac6ie, aac6if, aac6ig, aac6iia, aac6iib, aad9, aad9ib, aadd, acra, acrb, adea, adeb, adec, amra, amrb, ant2ia, ant2ib, ant3ia, ant4iia, ant6ia, aph33ia, aph33ib, aph3ia, aph3ib, aph3ic, aph3iiia, aph3iva, aph3va, aph3vb, aph3via, aph3viia, aph4ib, aph6ia, aph6ib, aph6ic, aph6id, arna, baca, bcra, bcrc, bl1_acc, bl1_ampc, bl1_asba, bl1_ceps, bl1_cmy2, bl1_ec, bl1_fox, bl1_mox, bl1_och, bl1_pao, bl1_pse, bl1_sm, bl2a_1, bl2a_exo, bl2a_iii2, bl2a_iii, bl2a_kcc, bl2a_nps, bl2a_okp, bl2a_pc, bl2be_ctxm, bl2be_oxy1, bl2be_per, bl2be_shv2, bl2b_rob, bl2b_tem1, bl2b_tem2, bl2b_tem, bl2b_tle, bl2b_ula, bl2c_bro, bl2c_pse1, bl2c_pse3, bl2d_lcr1, bl2d_moxa, bl2d_oxa10, bl2d_oxa1, bl2d_oxa2, bl2d_oxa5, bl2d_oxa9, bl2d_r39, bl2e_cbla, bl2e_cepa, bl2e_cfxa, bl2e_fpm, bl2e_y56, bl2f_nmca, bl2f_sme1, bl2_ges, bl2_kpc, bl2_len, bl2_veb, bl3_ccra, bl3_cit, bl3_cpha, bl3_gim, bl3_imp, bl3_l, bl3_shw, bl3_sim, bl3_vim, ble, blt, bmr, cara, cata10, cata11, cata12, cata13, cata14, cata15, cata16, cata1, cata2, cata3, cata4, cata5, cata6, cata7, cata8, cata9, catb1, catb2, catb3, catb4, catb5, ceoa, ceob, cml_e1, cml_e2, cml_e3, cml_e4, cml_e5, cml_e6, cml_e7, cml_e8, dfra10, dfra12, dfra13, dfra14, dfra15, dfra16, dfra17, dfra19, dfra1, dfra20, dfra21, dfra22, dfra23, dfra24, dfra25, dfra25, dfra25, dfra26, dfra5, dfra7, dfrb1, dfrb2, dfrb3, dfrb6, emea, emrd, emre, erea, ereb, erma, ermb, ermc, ermd, erme, ermf, ermg, ermh, ermn, ermo, ermq, ermr, erms, ermt, ermu, ermv, ermw, ermx, ermy, fosa, fosb, fosc, fosx, fusb, fush, ksga, lmra, lmrb, lnua, lnub, lsa, maca, macb, mdte, mdtf, mdtg, mdth, mdtk, mdtl, mdtm, mdtn, mdto, mdtp, meca, mecrl, mefa, mepa, mexa, mexb, mexc, mexd, mexe, mexf, mexh, mexi, mexw, mexx, mexy, mfpa, mpha, mphb, mphc, msra, norm, oleb, opcm, opra, oprd, oprj, oprm, oprn, otra, otrb, pbp1a, pbp1b, pbp2b, pbp2, pbp2x, pmra, qac, qaca, qacb, qnra, qnrb, qnrs, rosa, rosb, smea, smeb, smec, smed, smee, smef, srmb, sta, str, sul1, sul2, sul3, tcma, tcr3, tet30, tet31, tet32, tet33, tet34, tet36, tet37, tet38, tet39, tet40, teta, tetb, tetc, tetd, tete, tetg, teth, tetj, tetk, tetl, tetm, teto, tetpa, tetpb, tet, tetq, tets, tett, tetu, tetv, tetw, text, tety, tetz, Urc, tmrb, tolc, tsnr, vana, vanb, vanc, vand, vane, vang, vanha, vanhb, vanhd, vanra, vanrb, vanrc, vanrd, vanre, vanrg, vansa, vansb, vansc, vansd, vanse, vansg, vant, vante, vantg, vanug, vanwb, vanwg, vanxa, vanxb, vanxd, vanxyc, vanxye, vanxyg, vanya, vanyb, vanyd, vanyg, vanz, vata, vatb, vatc, vatd, vate, vgaa, vgab, vgba, vgbb, vph, ykkc, and ykkd (see the Antibiotic Resistance Genes Database (ARDB) available online).

In some embodiments, after successful production of the amplicons during the multiplex PCR assay, the resulting amplicons can be further processed to provide sequencing-ready amplicons. For example, some embodiments of the invention may comprise an indexing extension step. In some aspects, the indexing extension step may comprise extending the optimized multiplex amplicons using a set of indexing and common primers that recognize the respective universal tail sequences used for the particular group of amplicons in a minimal cycle PCR assay (e.g., 5-10 total cycles). In particular, each multiplex set of amplicons to be sequenced can be extended with a different set of index oligonucleotides and common oligonucleotides that recognize UT1 and UT2, respectively. In some aspects, the index sequence of the index oligonucleotides can be custom designed to allow for the selection of an index sequence from potentially thousands of different index sequences.

After this step, the resulting products include a set of amplicons for each sample/template that comprise the same index and any necessary sequences that may be required for a particular sequencing platform (e.g., platform sequences associated with the ILLUMINA® Next Generation sequencing platform). Thereafter, the resulting extension-reaction products can be quantified, pooled, and sequenced using a desired platform. In some aspects, the inclusion of the universal tail sequences on the index and common primers can coincide with the use of genomic and index read primers in the mixture of sequencing primer reagents. For example, some embodiments of the invention are capable of pooling multiple amplicons with multiple indices in a single sequencing run to provide 40,000×-95,000× coverage across the amplicons. In other embodiments, the systems and methods associated with the invention can be configured to provide any level of sequencing coverage that is desirable to the user (e.g., higher or lower that the coverage levels discussed above). In some embodiments, after sequencing and generation of the sequence data, the resulting data can be demultiplexed and the sequence files can be aligned to the appropriate references sequences for subsequent sequence analyses.

Some embodiments of the invention may comprise other applications. For example, some embodiments comprise an application of the universal tail sequences that could be used to detect clinically relevant RNA transcripts in a multiplex fashion. For example, RNA can be extracted from a sample, converted to cDNA using techniques known in the art, and the cDNA can function as the template for additional processes (e.g., multiplex PCR assays and subsequent sequencing). In some aspects, the amplicons resulting from the multiplex PCR reaction can be sequenced, in a manner as previously mentioned, and the resulting sequences can be aligned. As a result, differential numbers of sequence reads generated by the sequencing process (i.e., when aligned to the amplicon reference sequences), can provide data regarding the different copy numbers in the original RNA sample. As a result of this process, clinicians can gain an insight into the actual expression of a gene that is present. Specifically, virulence or resistance markers may display differential expression in a clinical sample. As such, understanding differential expression of these markers could be clinically relevant. Moreover, some embodiments could also be used to characterize population diversity using a relatively small set of markers from a very large number of samples, even within a single sample, which can enhance forensic applications.

In view of some conventional systems that require the addition of the index via ligation or an analogous method, some embodiments of the invention offer advantages. For example, by decoupling the marker-specific amplification from the addition of the indexes or indices, the marker-specific primers can be shorter and less prone to interactions with other primers, which can facilitate a true multiplex PCR reaction. As such, efficient amplification of multiple targets from very low quality and quantity DNA samples is enabled by this feature, which can be important for clinical and forensic samples. As a result of the use of some embodiments of the invention, clinical laboratories, using accessible sequencing technologies, would be able to rapidly detect the presence/absence of gene sequences within a patient sample that may impact treatment choice and/or clinical outcome, such as bacterial virulence genes or antibiotic resistance genes.

Embodiments of the invention offer additional advantages relative to conventional systems. For example, some embodiments of the invention comprise the use of PCR before sequencing such that only limited amounts of starting material are necessary and the starting material need not be of high quality (e.g., genomic DNA, crude DNA extracts, single stranded DNA, RNA, cDNA, etc.). In contrast, many conventional sample preparation systems may require relatively large amounts of starting material of relatively high quality, which can limit the use of these systems. Moreover, the inclusion of non-desirable template materials can also interfere in one or more downstream processes in conventional systems and methods. For example, if an investigation is being conducted that focuses on one or more organisms that may be associated with another organism (e.g., bacteria associated with a human), the sampling of the target organism may result in template contamination from the host organism.

In particular, in some aspects, obtaining samples of pathogenic or commensal bacteria from, on, or within a human may also result in the collection of human tissue. As such, when isolating the template, human nucleic acids may contaminate the bacterial template. Some embodiments of the invention are configured such that the contaminating template (e.g., from a human) would not interfere with downstream processes, including sequencing. For example, some embodiments of the invention operate such that only a limited amount of starting template (e.g., 500 femtograms or greater) can be used. Moreover, some embodiments are also configured such that the starting material (e.g., template contaminated with foreign nucleic acids) can still produce the required amplicons for sequencing in the presence of more than a 1,000-fold excess of contaminating template with no discernible inhibition of the multiplex PCR.

In certain aspects, the present invention provides an assay that works with as little as about 1 pg, about 900 fg, about 800 fg, about 700 fg, about 600 fg, about 500 fg, about 400 fg, about 300 fg, about 200 fg, or about 100 fg of genomic DNA.

In other aspects, the present invention provides methods that can be used on complex sample types. For example, a 6-plex assay described herein can be used to analyze tuberculosis sputum samples.

The methods described herein allow for new targets to easily be added due to Universal indexing oligonucleotides. Moreover, in some embodiments the multiplex reactions are optimized with SYBR qPCR using universal tail gene-specific primers, for example.

In yet other embodiments, several multiplex reactions from the same sample can be pooled and indexed prior to sequencing. The current invention also allows for flexible scale and read lengths, on multiple platforms.

In some embodiments, the methods described herein are applied for quantitative analysis including the detection of gene copy number and targeted RNAseq.

In certain aspects, a synthetic plasmid is used as an internal positive PCR sequencing control.

The methods and assays of the present invention have various applications. Among these applications is an assay for *Mycobacterium tuberculosis* (Mtb). In one embodiment, this Mtb assay comprises a six-plex antibiotic resistance gene SNP variant sequencing assay.

The methods and assays described herein can also be used to analyze and sequence DNA from *Burkholderia pseudomallei* with, for example, 7-, 6- and 5-plex species specific amplicon multiplex assays.

In certain embodiments, the present invention comprises a 16S rRNA and/or an Internal Transcribed Spacer (ITS) amplicon assay. These assays can be used in a variety of clinical sample types and with samples containing the bacterial pathogen, *Leptospira*.

In some embodiments, the present invention comprises a major histocompatibility complex (MHC) amplicon assay. In one embodiment, the MHC amplicon assay is used with samples from Prairie Dogs.

In other aspects, the methods and assays of the present invention comprise species specific amplicon assays in several clinically important pathogens and/or antibiotic resistance gene multiplex assays covering a variety of important genes.

EXAMPLES

Herein below are set forth various embodiments of the present invention. It is anticipated that suitable modifications can be made thereto which will nonetheless remain within the scope of the invention. The invention shall therefore only be construed in accordance with the claims below and not any particular embodiment or example.

Example 1

Figure 1B:
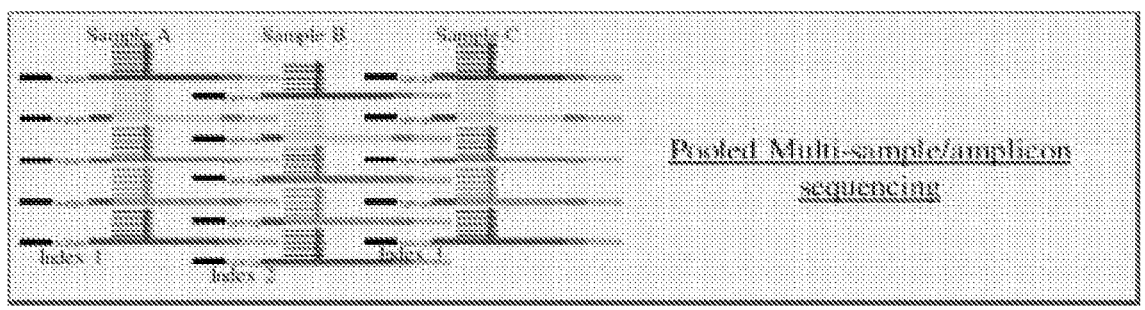
FIG. 1B shows pooled multi-sample/amplicon sequencing.
Figure 1C:
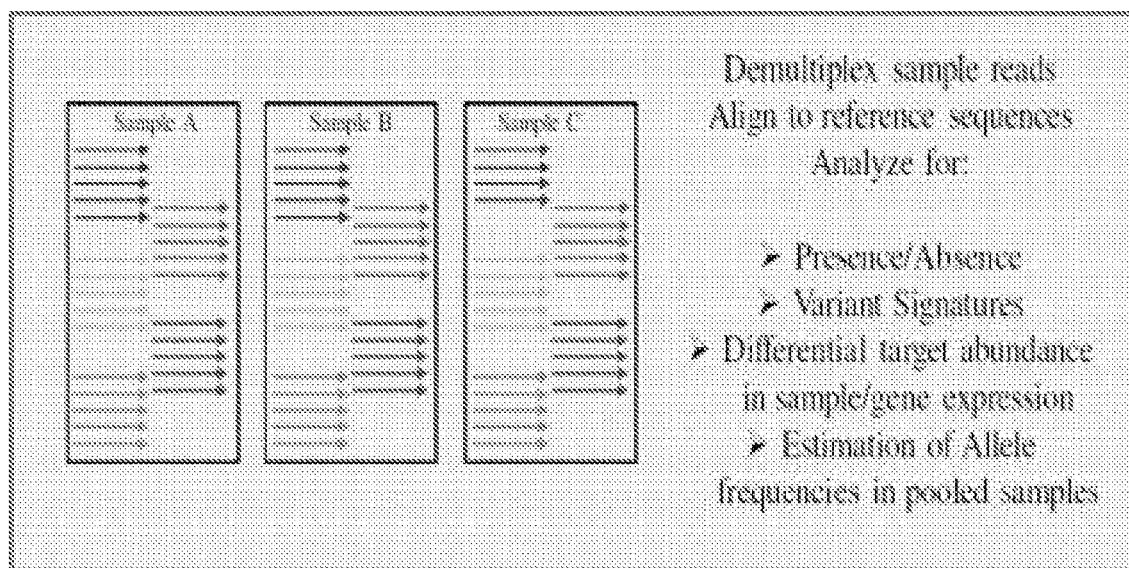
FIG. 1C shows demultiplexing of sample reads, alignment to reference sequences, and subsequent analysis.
Figure 3:
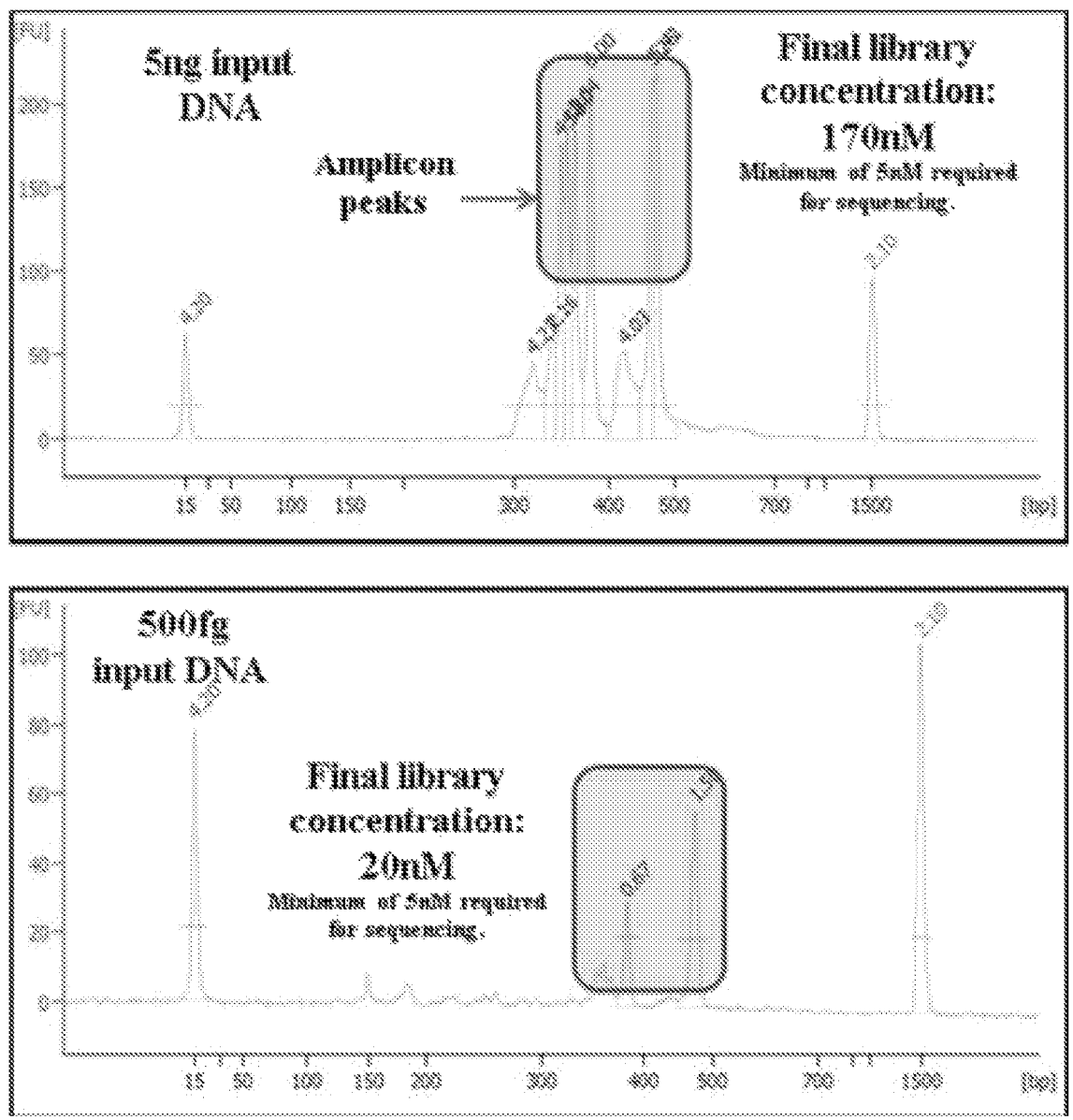
FIG. 3 is a series of output graphs from an AGILENT BIOANALYZER® that detail the resulting concentrations of amplicons produced using 5 ng and 500 fg of input template using some embodiments of the invention.

Universal Multiplex Indexing Strategy for ILLUMINA® Next Generation Amplicon Sequencing Process Referring to FIGS. 1 and 2, embodiments of the invention can be used as a universal multiplex indexing strategy for the ILLUMINA® Next Generation amplicon sequencing process. As used in this example, a multiplex PCR is performed with a total of five amplicons per reaction contemplated. In particular, each amplicon is considered to be associated with a different marker (e.g., antibiotic resistance genes). As such, to amplify each marker, the PCR reaction mixture is provided with five unique forward primers and five unique reverse primers (i.e., each primer designed to bind to a marker-specific sequence). Moreover, as shown in FIG. 1, the forward primers comprise a first universal tail sequence (UT1) at the 5' end of the respective primers, with the universal tail sequence being identical for each of the forward primers in the reaction mixture. Similarly, the reverse primers comprise a second universal tail sequence (UT2) at the 5' end of the respective primers, with the second universal tail sequences being identical for each of the reverse primers in the mixture, but different than the sequence of UT1. The sequences associated with UT1 and UT2 (and other potential sequences for universal tails, UT3 and UT4) are recited in FIG. 2. Moreover, as illustrated in FIG. 3, the multiplex PCR system using the universal tail sequences and marker-specific primers produces high-quality amplicons when the amount of input template is as low as 500 femtograms. Even this de minimis amount of starting material provides a sufficient concentration of amplicon for downstream processes.

After completion of the initial multiplex PCR, the assay mixture comprises five amplicons that include the desired marker-specific amplicon with UT1 and UT2 integrated into the ends of the amplicons, as illustrated in FIG. 1. Thereafter, the five resulting amplicons are extended using platform-specific primers that recognize UT1 and UT2 for adding the indexes to each amplicon. In particular, as illustrated in FIG. 2, index-extension primers were designed that recognize at least one of UT1 and UT2. The index-extension primers also include Next Generation sequencing-specific elements, including the index and the read primer sequences that are used during the sequencing process. This extension process occurs during a simplified PCR reaction that uses an abbreviated cycle process, such as 5-10 total cycles of amplification. In particular, FIG. 2 also includes a list of potential index-extension primers that have been designed to recognize at least one of the universal tail sequences.

After completion of the extension process, the resulting modified amplicons are pooled and sequenced. For example, as shown in FIG. 1, samples from multiple multiplex PCR reactions can be pooled together for a single sequencing event. In particular, each multiplex PCR assay mixture may contain the template from a single organism such that each of the amplicons provides data regarding that particular organism. In addition, the same multiplex PCR reaction can be performed on multiple templates from multiple samples in multiple reaction vessels at the same time such that amplicons of the same five markers are amplified from each respective template. However, in order to differentiate between the sources of the amplicons upon pooling, during the extension step, unique indexes can be integrated into amplicons that originate from different organisms. For example, if ten different clinical isolates of bacteria are being tested with the amplification of five markers for each of the ten isolates, then a different index is integrated into the five amplicons that originate from a given isolate (i.e., each of the amplicons originating from the isolate will have the same index, which will differ from the index associated with the remaining nine isolates). As a result, the samples can be pooled for sequencing during a single sequencing run and distinguished based on the index sequence during analysis of the data. In particular, after sequencing, the resulting data can be demultiplexed and aligned to a reference sequence (e.g., a wild type sequence and/or other alleles for each of the respective markers). As a result, the aligned sequences can be analyzed for the presence or absence of markers, variant signatures associated with the markers, differential marker presence in the sample, which includes the capability of analyzing gene expression, and an estimate of allele frequencies of various alleles of the markers in the pooled samples.

Example 2

Universal Tail Amplicon Sequencing Assay for Use with Samples Containing *Mycobacterium tuberculosis*

The following protocol was used to prepare and sequence amplicons from samples containing *Mycobacterium tuberculosis*.

Target Amplification

Primer sets targeting *Mycobacterium tuberculosis* gene regions were used (see Table 1). The target amplicons were between 180-400 bp long. The size of the amplicons was dependent on the positions of the SNPs and the constraints of the length of the sequencing read. Along with organism specific sequence, each primer has a universal tail sequence (bold sequences in Table 1). All forward primers have one universal tail sequence while all the reverse primers have a second universal tail sequence. In Gene Specific multiplex PCR reactions, all target amplicons are synthesized with the universal tail sequence added to the amplicons. The PCR parameters are as follows: initial denaturation at 98° C. for 1 min, twenty-five cycles of denaturation at 98° C. for 10 sec, annealing at 60° C. for 15 sec, and extension at 72° C. for 20 sec and a final extension at 72° C. for 2 min. A single 25 uL PCR reaction containing 2 uL of DNA, 12.5 uL of Q5® Hot Start High-Fidelity 2x Master Mix (New England Biolabs® Inc.), 4 uL of a primer mix, 1.5 uL of molecular grade H₂O, and 5 uL of 5M Betaine solution (Sigma-Aldrich®). After PCR the reaction is cleaned up using a 1× Agencourt® AMPure® XP bead (Beckman Coulter) clean up with elution in 25 uL of a 10 mM Tris-HCl 0.05% Tween 20 solution.

Index Extension-Library Creation

A second PCR adds a specific index sequence, based on the Kozarewa and Turner 8 bp indexing scheme (see Kozarewa I, Turner D. 96-Plex Molecular Barcoding for the Illumina Genome Analyzer. In: Kwon Y M, Ricke S C, editors. High-Throughput Next Generation Sequencing: Humana Press; 2011. p. 279-98.), to the amplicons using the universal tail sequences on either end of the amplicon. At the end of the Index Extension PCR there is a sequencer ready amplicon library. The PCR parameters are as follows: initial denaturation at 98° C. for 2 min, six cycles of denaturation at 98° C. for 30 sec, annealing at 60° C. for 20 sec, and extension at 72° C. for 30 sec and a final extension at 72° C. for 5 min. A single 50 uL PCR reaction containing 2 uL of template, 25 uL of 2×KAPA HiFi HotStart ReadyMix (KAPA Biosystems), 2 uL of the 10 uM common universal tail primer, 2 uL of 10 uM specific index universal tail primer, 9 uL of molecular grade H₂O, and 10 uL of 5M Betaine solution (Sigma-Aldrich®). After PCR the reaction was cleaned using a 0.8× Agencourt® AMPure® XP bead (Beckman Coulter) clean up with elution in 40 uL of a 10 mM Tris-HCl 0.05% Tween 20 solution to remove primer dimers. All completed libraries were run on the Bioanalyzer® 2100 (Agilent Technologies®) for confirmation of target amplification.

Pooling and Sequencing

Figure 4:
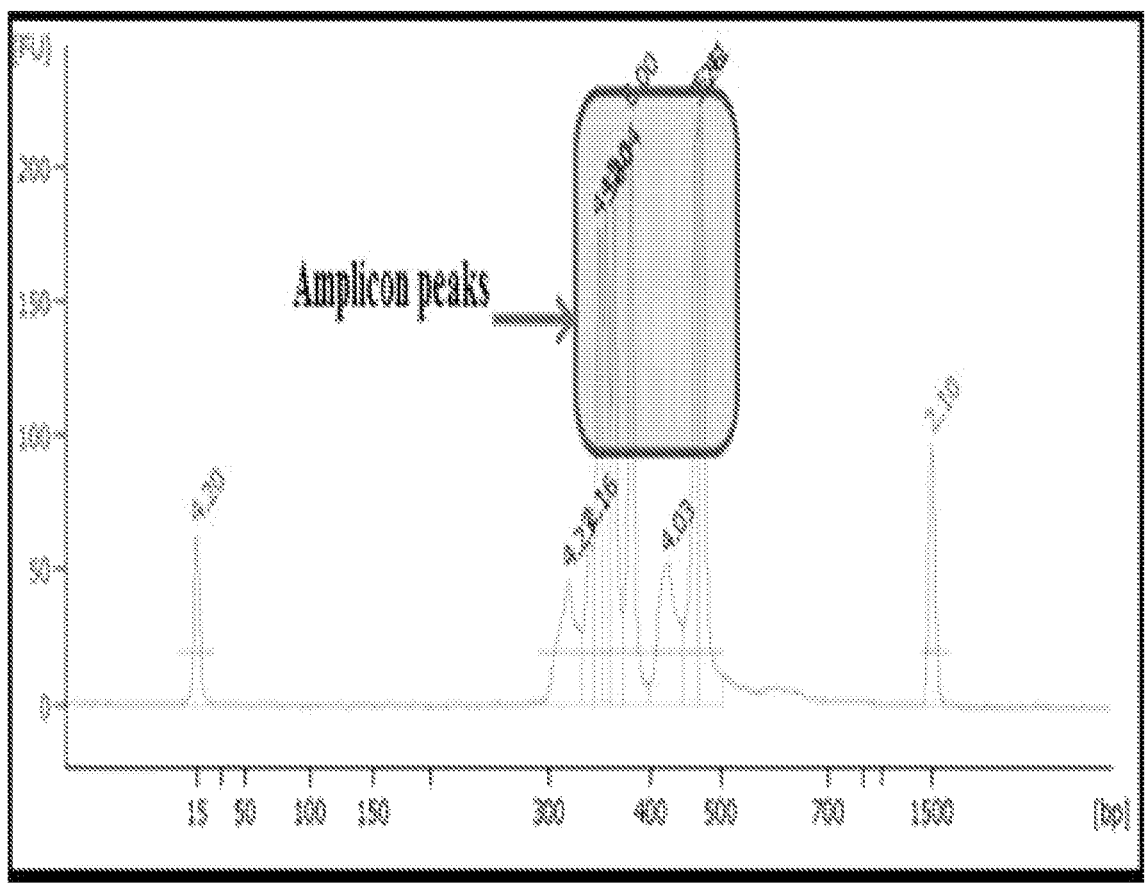
FIG. 4 presents an AGILENT BIOANALYZER® analysis with a six-plex *Mycobacterium tuberculosis* (Mtb) antibiotic resistance gene amplicon sequencing assay. The chromatogram depicts analysis of a multiplex amplification reaction after amplicon yield optimization.

By adding sample specific index sequences to the amplicons, pools of several samples are made for sequencing. Each individual library is quantified using KAPA Library Quantification Kit—Illumina/ABI Prism® (KAPA Biosystems) qPCR, and pooled in equal molar concentrations. At least 25% of each sequencing run was filled with whole genome or PhiX control samples to ensure base diversity and reduce complications with sequencing. For the validation a single sequencing pool was sequenced on the Illumina® MiSeq platform using 2×300 bp version 3 sequencing chemistry (Illumina®). If PhiX control was not used for base diversity (e.g., at 25% of a sequencing run), then it was spiked in a low concentrations (i.e., 1-5%) in each run for error rate examination. Novel Read 1, Read 2, and indexing sequencing primers were used for sequencing (see SEQ ID NOs: 6, 7, and 8 in FIG. 2). A representative chromatogram depicting an analysis of a multiplex amplification reaction after amplicon yield optimization is shown in FIG. 4.

TABLE 1

*M. tuberculosis* specific primers with universal tail sequences. All oligos are with standard de-salting. The universal tail sequences are highlighted in bold with the forward primer sequence differing from the reverse primer sequence.

| Forward Primer | SEQ ID NO: | Sequence |
| --- | --- | --- |
| gyrAv2fUT1 | 45 | ACCCAACTGAATGGAGCGGGTGCTCTATGCAATGTTCGAT |
| eisv2fUT1 | 46 | ACCCAACTGAATGGAGCCGTCACCGCAGATCCATGTAC |
| rpoBv2fUT1 | 47 | ACCCAACTGAATGGAGCCGATCACACCGCAGACGTT |

TABLE 1-continued

*M. tuberculosis* specific primers with universal tail sequences. All oligos are with standard de-salting. The universal tail sequences are highlighted in bold with the forward primer sequence differing from the reverse primer sequence.

| | SEQ ID NO: | Sequence |
|---|---|---|
| katGv2fUT1 | 48 | ACCCAACTGAATGGAGCCCATGAACGACGTCGAAACAG |
| inhAv2fUT1 | 49 | ACCCAACTGAATGGAGCCCTCGCTGCCCAGAAAGG |
| rrsv2fUT1 | 50 | ACCCAACTGAATGGAGCCTAGTAATCGCAGATCAGCAACG |

| Reverse Primer | SEQ ID NO: | Sequence |
|---|---|---|
| gyrAv2rUT2 | 51 | ACGCACTTGACTTGTCTTCGGGCTTCGGTGTACCTCATC |
| eisv2rUT2 | 52 | ACGCACTTGACTTGTCTTCCGTCGCTGATTCTCGCAGTG |
| rpoBv2rUT2 | 53 | ACGCACTTGACTTGTCTTCGTTTCGATCGGGCACATCC |
| katGv2rUT2 | 54 | ACGCACTTGACTTGTCTTCGCTCTTCGTCAGCTCCCACTC |
| inhAv2rUT2 | 55 | ACGCACTTGACTTGTCTTCGTCACATTCGACGCCAAACAG |
| rrsv2rUT2 | 56 | ACGCACTTGACTTGTCTTCGCCTACGCCCCACCAGTT |

Example 3

Universal Tail Amplicon Sequencing Assay for Use with Samples Containing *Burkholderia pseudomallei* and *Burkholderia mallei*

The protocol outlined in Example 2 was used to prepare and sequence amplicons from samples containing *Burkholderia pseudomallei* and *Burkholderia mallei*.

The primers specific to *Burkholderia pseudomallei* and *Burkholderia mallei* are outlined in Table 2.

Figure 5:
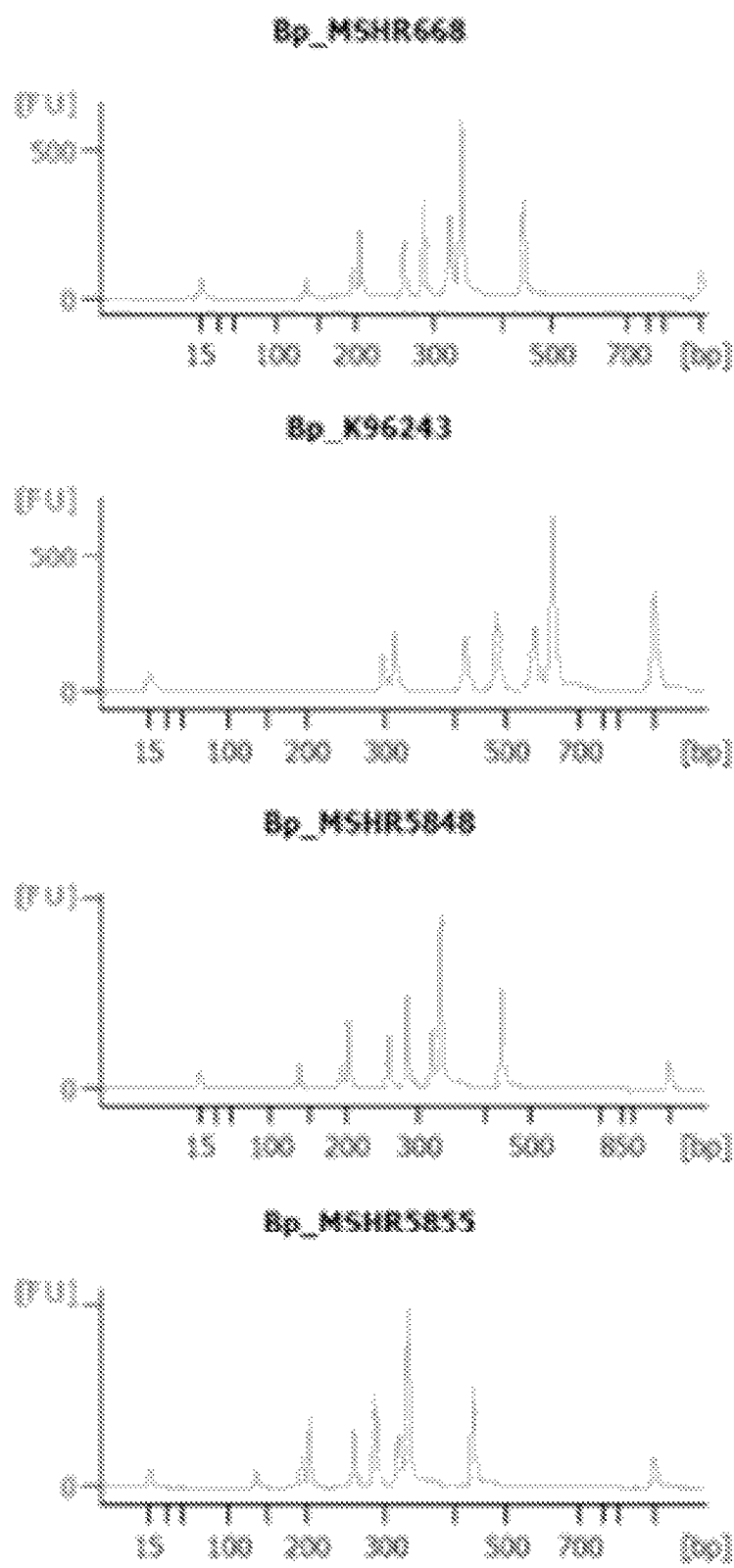
FIG. 5 depicts AGILENT BIOANALYZER® chromatograms from a universal tail (UT) amplicon six-plex assay for 11 diverse *Burkholderia pseudomallei* strains and 1 *Burkholderia mallei* strain. Arrows in the Bp_406e panel indicate peaks corresponding to each amplicon.
Figure 5:
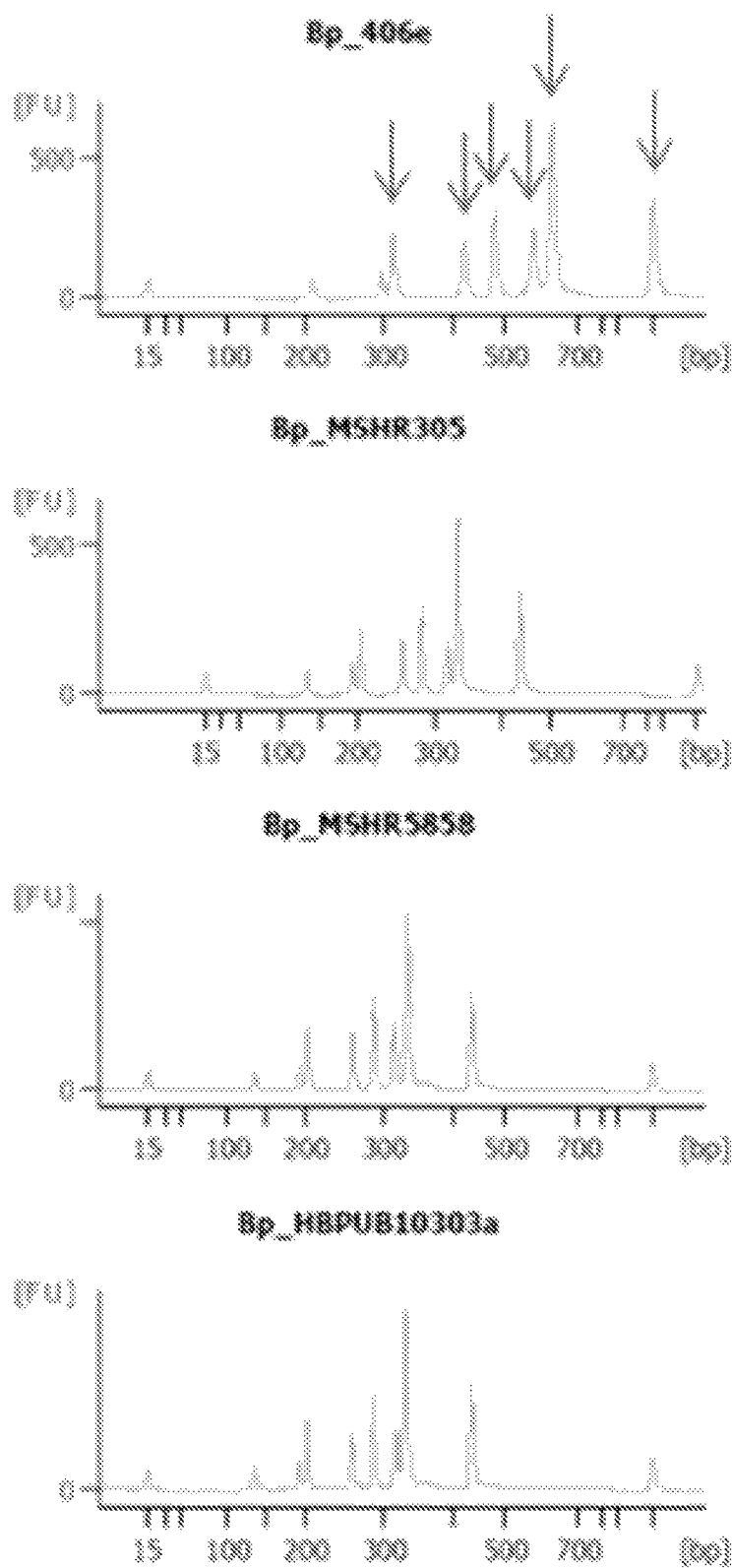
Figure 5:
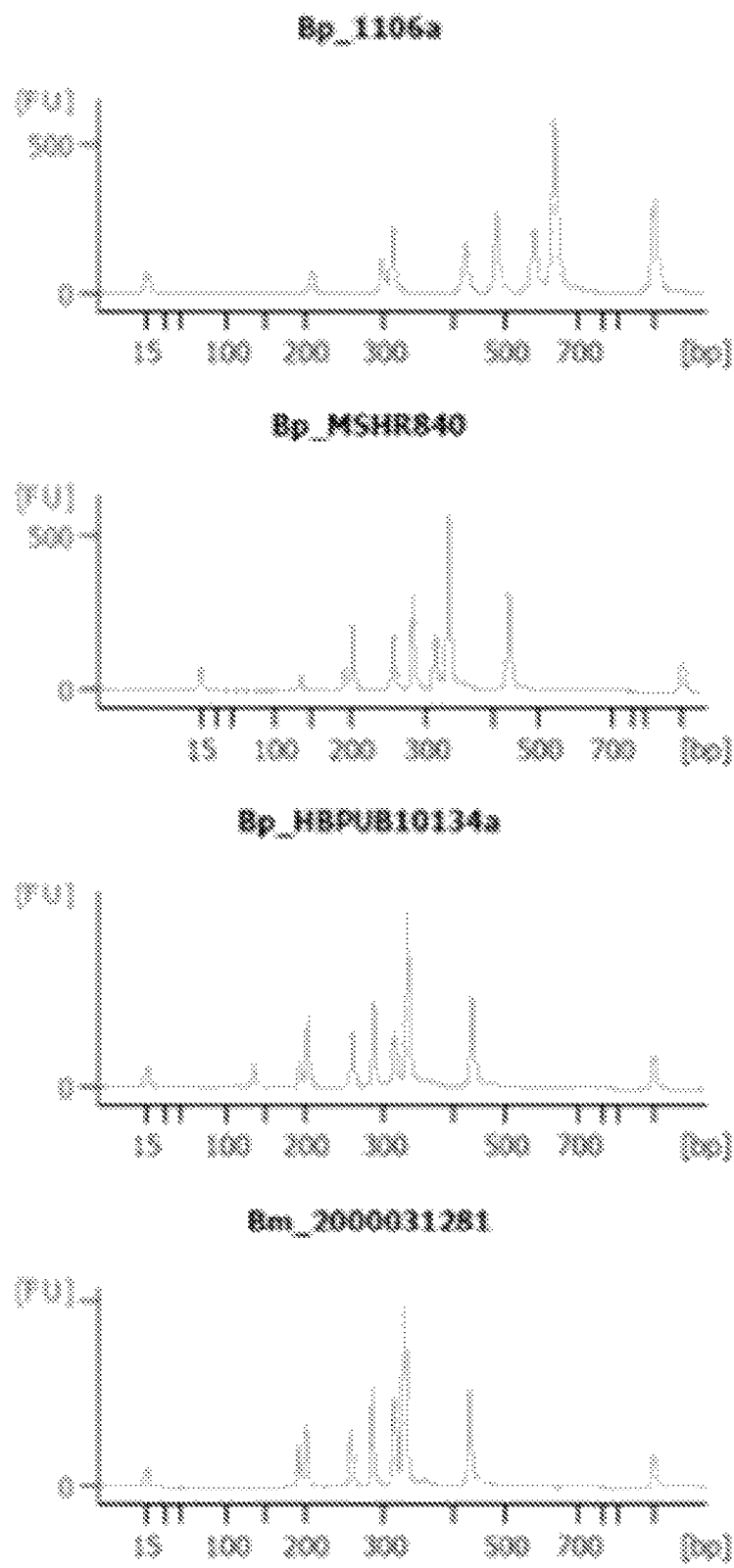

FIG. 5 shows consistent PCR amplification and Illumina® index extension (peaks on chromatogram) for 12 diverse *Burkholderia pseudomallei* and *Burkholderia mallei* isolate DNA samples, using the oligos listed in Table 2 in a multiplex fashion.

Twelve genomic DNA samples were amplified using the Bp/Bm UT multiplex amplicon assay. Arrows in the Bp_406e panel indicate peaks corresponding to each amplicon. Optimal amplification occurred in all 12 samples Sizing standards failed during the run, but relative peak sizes and migration rates indicate successful amplification in all samples. Sequencing resulted in ~4 fold variance in read counts among all amplicons and recovery of correct sequence.

TABLE 2

*Burkholderia pseudomallei* and *Burkholderia mallei* specific primers with universal tail sequences.

| UT Forward Oligo Name | SEQ ID NO: | UT Forward Oligo Sequence |
|---|---|---|
| UT2-BpCEN322640-f2 | 57 | ACGCACTTGACTTGTCTTCCGCGGACAGCATCGATTACGTGAATC |
| UT1-BpCEN1761486-f1 | 58 | ACCCAACTGAATGGAGCGACCTGCAGCAGGTATTCGACATTATCGTTC |
| UT2-BpCEN1722622-f1 | 59 | ACGCACTTGACTTGTCTTCCAACGGGCGAGTTTGCAACGGAATC |
| UT1-BpCEN1565214-f1 | 60 | ACCCAACTGAATGGAGCCTGACCGAACGATGGCTGGAGATACATGC |
| UT2-BpCEN894337-f1 | 61 | ACGCACTTGACTTGTCTTCCGAAAATAATTTTCGGCCGGCGCAC |
| UT2-BpCEN1235988-f1 | 62 | ACGCACTTGACTTGTCTTCGCGCTGCCCGTTTCACCACTGG |

| UT Reverse Oligo Name | | UT Reverse Oligo Sequence |
|---|---|---|
| UT1-BpCEN32264-r2 | 63 | ACCCAACTGAATGGAGCCCGCCGAATCCGATGCTCAATTTC |
| UT2-BpCEN1761486-r1 | 64 | ACGCACTTGACTTGTCTTCAGCTTCGCATACAGCACTTCCGCCAG |
| UT1-BpCEN1722622-r1 | 65 | ACCCAACTGAATGGAGCGCCGGCTTGGCTTCGTCCTTGTC |
| UT2-BpCEN1565214-r1 | 66 | ACGCACTTGACTTGTCTTCCAAATGGGAAGCGAGCTCCCTTCCGA |
| UT1-BpCEN894337-r1 | 67 | ACCCAACTGAATGGAGCCGACAGGCATCGGGCGACTACTACCAG |
| UT1-BpCEN1235988-r1 | 68 | ACCCAACTGAATGGAGCCGTGACGCCGTCGGGAAAGATCATC |

Example 4

Figure 7:
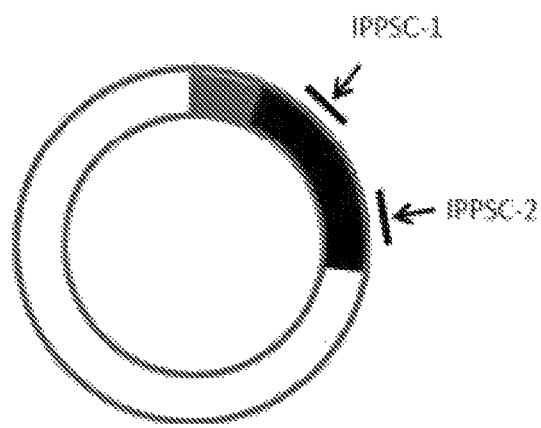
FIG. 7 depicts an internal positive PCR and sequencing control for universal tail amplicon sequencing.

Internal Positive PCR and Sequencing Control for Universal Tail Amplicon Sequencing Assay The schematic in FIG. 7 depicts a plasmid construct containing a synthetic 1000 bp sequence (shown in black) around which two different amplicons have been designed (IPPSC-1, IPPSC-2.) This sequence displays no significant BLAST similarity to any sequences in the NCBI nucleotide database. This synthetic plasmid DNA template can be used in conjunction with the Universal Tail target specific oligo sequences shown in Table 3 below to act as an internal positive PCR and sequencing control, to indicate both successful PCR amplification and subsequent amplicon sequencing in any Universal Tail Amplicon Sequencing Assay.

to the pre-amplified starting template, indicating that the relative sequence read counts also strongly correlate ($R^2$=0.98) to the relative concentration of the starting template target concentrations.

The amplification comparison of transcriptome RNA-Seq analysis with UT amplicon sequencing RNA-Seq analysis using samples containing *Burkholderia pseudomallei* confirmed the utility of the Universal Tail Amplicon Sequencing Assay in targeted RNA-Seq (see FIG. 6B). Briefly, the *Burkholderia* multiplex (see Table 2) was used in a multiplex reverse transcriptase reaction to generate amplicon sequence from *Burkholderia* RNA samples from a previous RNAseq study. Normalized read counts from the targets from the original study were compared to the UT amplicon sequence data. While not as highly correlated as the mock mixture experiment (FIG. 6A), the relative read counts were

TABLE 3

Primers for internal positive PCR and sequencing control.

| UT Forward Oligo Name | SEQ ID NO: | UT Forward Oligo Sequence |
|---|---|---|
| UT1-IPSC-f1 | 69 | ACCCAACTGAATGGAGCGGGCGGACGAAAACCCTTGAGCACAG |
| UT1-IPSC-f2 | 70 | ACCCAACTGAATGGAGCGCGGCAGCCGTTGAGGCAAAAGTGATAC |

| UT Reverse Oligo Name | | UT Reverse Oligo Sequence |
| UT2-IPSC-r1 | 71 | ACGCACTTGACTTGTCTTCGCCGGGATGCCTTACCTAGACGCAATGA |
| UT2-IPSC-r2 | 72 | ACGCACTTGACTTGTCTTCCGAGTTCCGTCCGGTTAAGCGTGACAGTC |

Example 5

Quantitative Analysis with the Universal Tail Amplicon Sequencing Assay

The Universal Tail Amplicon Sequencing Assay can also be used to perform quantitative analysis to determine gene copy number, for example. In addition, the assay can be used to perform targeted RNA-Seq.

Figure 6A:
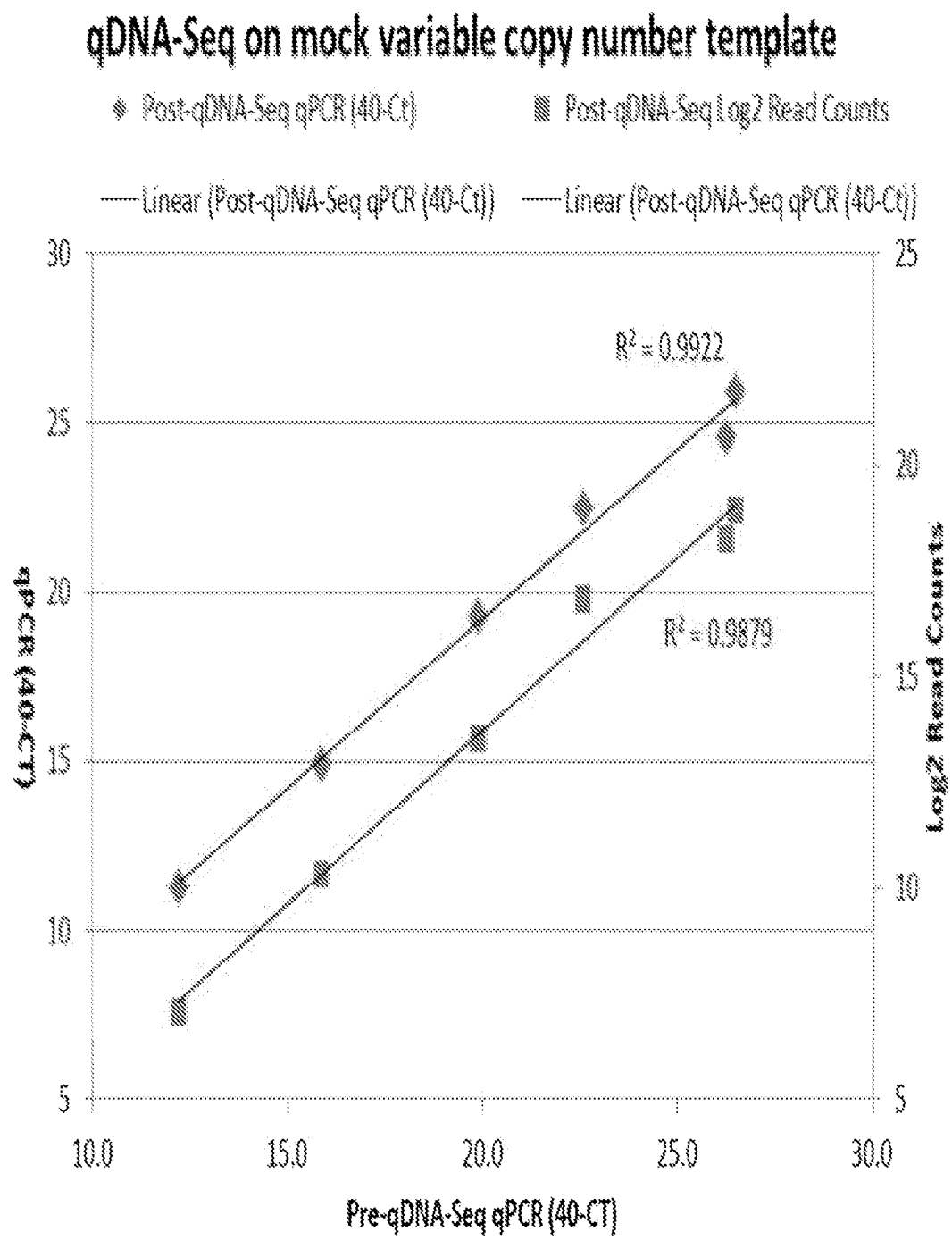
FIG. 6A depicts a quantitative DNA Sequencing (qDNA-Seq) analysis on a mock variable copy number template.

To demonstrate the assay's potential for quantitative analysis a quantitative DNA sequencing (qDNA-Seq) experiment was performed with a mock variable copy number template. The results in FIG. 6A demonstrate the assay's capability to detect variations in gene copy number.

Briefly, individual Mtb amplicon targets that comprise the Mtb multiplex (see Table 1) were mixed together at different concentrations across four orders of magnitude and then used as template for the Mtb multiplex Universal Tail Amplicon Sequencing Assay. Gene specific qPCR on the artificial mixture pre-(x axis) and post-(left y axis) amplification shows strong correlation ($R^2$=0.99), indicating the relative variable concentrations of each target is maintained after the multiplex amplification. The multiplex amplification was then sequenced on a Illumina® MiSeq platform. The right y axis shows the sequence read counts that aligned to each of the target sequences, $\log_2$ transformed, compared still highly correlated (($R^2$=0.89). These studies indicate the potential for quantitative analysis using the Universal Tail Amplicon Sequencing methodology.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

Figure 6B:
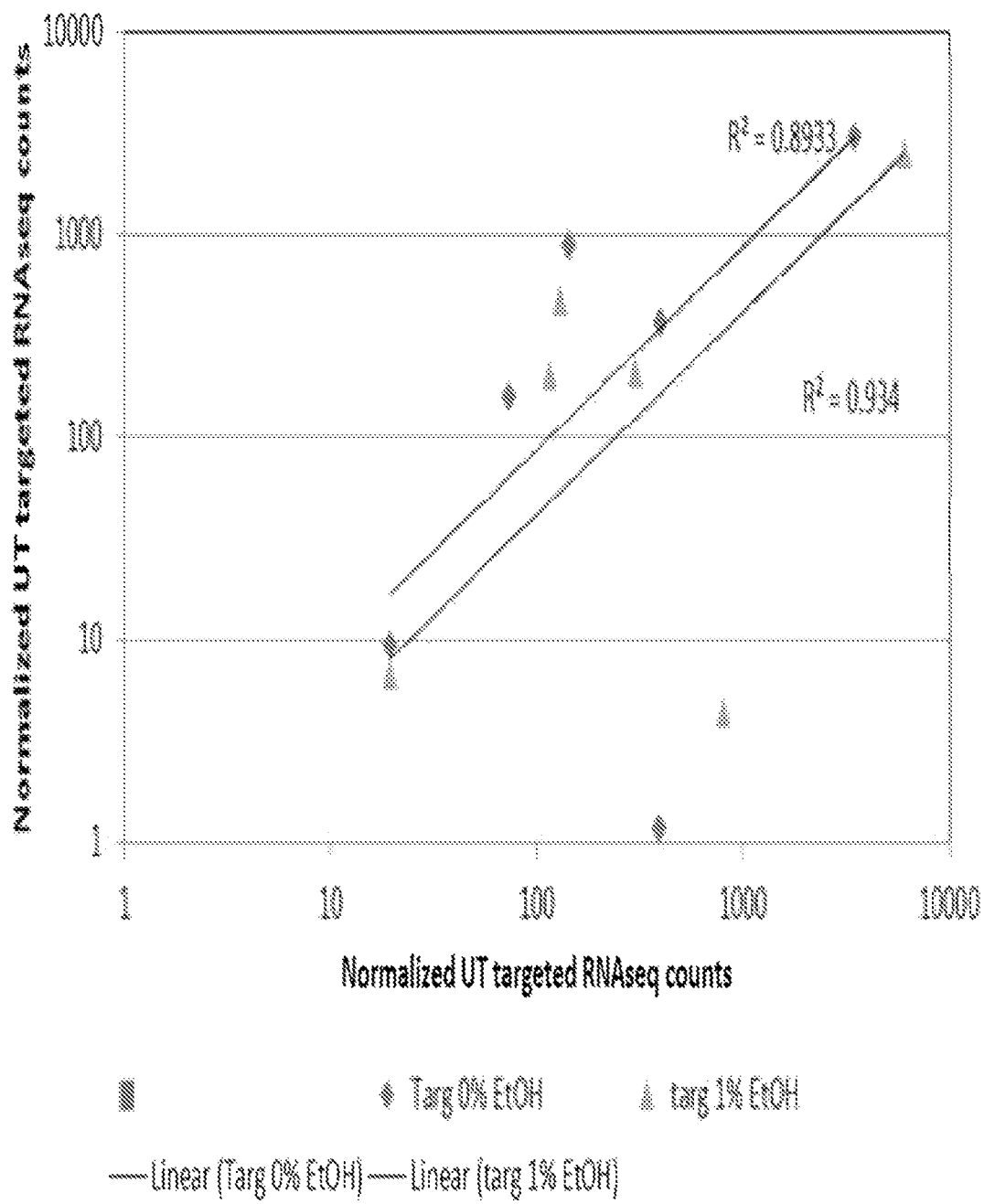
FIG. 6B depicts a comparison of transcriptome RNAseq analysis vs. targeted UT amplicon sequencing RNAseq analysis in a *Burkholderia pseudomallei* six-plex amplicon multiplex assay.

What is claimed is:

1. A sequencing method comprising the steps of:

receiving a sample;

amplifying at least a first marker within the sample to produce at least a first amplicon, wherein the step of amplifying at least the first marker comprises mixing the sample with a first oligonucleotide comprising a first universal tail sequence and a second oligonucleotide comprising a second universal tail sequence, wherein the first universal tail sequence and the second oligonucleotide sequence are different;

adding an index to at least the first amplicon using an indexing oligonucleotide to produce at least a first indexed amplicon, wherein the indexing oligonucleotide comprises an index sequence and a complementary sequence that recognizes at least one of the first universal tail sequence and the second universal tail sequence, and the step of adding an index to the first amplicon comprises mixing the first amplicon with the at least one indexing oligonucleotide; and sequencing the indexed amplicon with at least one sequencing primer, wherein at least one sequencing primer comprises a sequence selected from the group consisting of SEQ ID NO: 6, SEQ ID NO: 7, and SEQ ID NO: 8.

2. The method of claim 1, wherein the first universal tail sequence and the second universal tail sequence independently comprise a sequence selected from the group consisting of SEQ ID NO: 1, SEQ ID NO: 2, SEQ ID NO: 3, and SEQ ID NO: 4.

3. The method of claim 1, further comprising:

amplifying a second marker to produce a second amplicon by mixing the sample with a third oligonucleotide comprising the first universal tail sequence and a fourth oligonucleotide comprising the second universal tail sequence; and adding the index to the second amplicon using the indexing oligonucleotide to produce a second indexed amplicon, wherein the step of adding an index to the second amplicon comprises mixing the second amplicon with the at least one indexing oligonucleotide.

4. The method of claim 3, wherein the steps of amplifying the first marker and the second marker occur in a multiplex polymerase chain reaction.

5. The method of claim 1, wherein the at least one indexing oligonucleotide comprises a complementary sequence that recognizes at least one of the first universal tail sequence and the second universal tail sequence at the 3' end and the index sequence at the 5' end.

6. The method of claim 5, wherein the at least one indexing oligonucleotide comprises a sequence selected from the group consisting of SEQ ID NOs: 9-44.

7. The method of claim 1, wherein the sample comprises a pathogenic organism selected from the group consisting of *Mycobacterium tuberculosis, Burkholderia pseudomallei, Burkholderia mallei*, and *Leptospira* sp.

8. The method of claim 1, wherein the first marker comprises an antibiotic resistance gene.

9. The method of claim 1, wherein the sample comprises castor beans, castor bean derivatives, and/or tissue from a human.

10. A method of producing sequencing platform-ready amplicons from a sample, the method comprising the steps of:

receiving a sample;

amplifying at least a first marker within the sample to produce at least a first amplicon, wherein the step of amplifying at least the first marker comprises mixing the sample with a first oligonucleotide comprising a first universal tail sequence and a second oligonucleotide comprising a second universal tail sequence, wherein the first universal tail sequence and the second oligonucleotide sequence are different; and adding an index to at least the first amplicon using an indexing oligonucleotide to produce at least a first indexed amplicon, wherein the indexing oligonucleotide comprises a sequence selected from the group consisting of SEQ ID NOs: 9-44, the step of adding an index to the first amplicon comprises mixing the first amplicon with the at least one indexing oligonucleotide, and the indexed amplicon is sequencing ready.

11. The method of claim 10, wherein the first universal tail sequence and the second universal tail sequence independently comprise a sequence selected from the group consisting of SEQ ID NO: 1, SEQ ID NO: 2, SEQ ID NO: 3, and SEQ ID NO: 4.

12. The method of claim 10, further comprising:

amplifying a second marker to produce a second amplicon by mixing the sample with a third oligonucleotide comprising the first universal tail sequence and a fourth oligonucleotide comprising the second universal tail sequence; and adding the index to the second amplicon using the indexing oligonucleotide to produce a second indexed amplicon, wherein the step of adding an index to the second amplicon comprises mixing the second amplicon with the at least one indexing oligonucleotide.

13. The method of claim 12, wherein the steps of amplifying the first marker and the second marker occur in a multiplex polymerase chain reaction.

14. The method of claim 10, wherein the sample comprises a pathogenic organism selected from the group consisting of *Mycobacterium tuberculosis, Burkholderia pseudomallei, Burkholderia mallei*, and *Leptospira* sp.

15. The method of claim 10, wherein the first marker comprises an antibiotic resistance gene.

16. The method of claim 10, wherein the sample comprises castor beans, castor bean derivatives, and/or tissue from a human.

17. The method of claim 10, further comprising sequencing the indexed amplicon with at least one sequencing primer.

18. The method of claim 17, wherein the sequencing primer comprises a sequence selected from the group consisting of SEQ ID NO: 6, SEQ ID NO: 7, and SEQ ID NO: 8.

* * * * *